(12) United States Patent
Cohen et al.

(10) Patent No.: US 10,208,133 B2
(45) Date of Patent: Feb. 19, 2019

(54) SITE-SELECTIVE MODIFICATION OF POLYSACCHARIDES AND APPLICATIONS THEREOF

(71) Applicant: B. G. Negev Technologies and Applications Ltd., Beer-Sheva (IL)

(72) Inventors: Smadar Cohen, Beer-Sheva (IL); Ashraf Brik, Beer-Sheva (IL)

(73) Assignee: B.G. NEGEV TECHNOLOGIES AND APPLICATIONS LTD., Beer Sheva (IL)

( * ) Notice: Subject to any disclaimer, the term of this patent is extended or adjusted under 35 U.S.C. 154(b) by 0 days.

(21) Appl. No.: 15/315,770

(22) PCT Filed: Jun. 1, 2015

(86) PCT No.: PCT/IL2015/050562
§ 371 (c)(1),
(2) Date: Dec. 2, 2016

(87) PCT Pub. No.: WO2015/186127
PCT Pub. Date: Dec. 10, 2015

(65) Prior Publication Data
US 2017/0096500 A1     Apr. 6, 2017

Related U.S. Application Data

(60) Provisional application No. 62/006,307, filed on Jun. 2, 2014.

(51) Int. Cl.
| | | |
|---|---|---|
| A61K 38/00 | (2006.01) |
| C08B 37/08 | (2006.01) |
| C08B 37/00 | (2006.01) |
| C08B 37/02 | (2006.01) |
| C07K 14/47 | (2006.01) |
| C07K 9/00 | (2006.01) |

(52) U.S. Cl.
CPC .......... *C08B 37/0072* (2013.01); *C07K 9/001* (2013.01); *C07K 14/4747* (2013.01); *C08B 37/00* (2013.01); *C08B 37/003* (2013.01); *C08B 37/0021* (2013.01); *C08B 37/0084* (2013.01)

(58) Field of Classification Search
None
See application file for complete search history.

(56) References Cited

FOREIGN PATENT DOCUMENTS

| WO | 03024984 A1 | 3/2003 |
| WO | 2011163568 A1 | 12/2011 |

OTHER PUBLICATIONS

Lees et al; "Versatile and efficient synthesis of protein-polysaccharide conjugate vaccines using aminooxy reagents and oxime chemistry" Vaccine 24 pp. 716-729. (2006).
Sestak et al; "Single-Step Grafting of Aminooxy-Peptides to Hyaluronan: A Simple Approach to Multifunctional Therapeutics for Experimental Autoimmune Encephalomyelitis" J Control Release.168(3): pp. 334-340. (2013).
Garaneger et al; "New Multifunctional Molecular Conjugate Vector for Targeting, Imaging, and Therapy of Tumors" Molecular Therapy vol. 12, No. 6, pp. 1168-1175 .(2005).
Bondalapati et al; "Rapid End-Group Modification of Polysaccharides for Biomaterial Applications in Regenerative Medicine" Macromol. Rapid Commun. 35, pp. 1754-1762. (2014).
Ulrich et al; "Oxime Ligation: A Chemoselective Click-Type Reaction for Accessing Multifunctional Biomolecular Constructs" Chem. Eur. J. 20, 3pp.4-41. (2014).
Renaudet et al;"Chemoselectively template-assembled glycoconjugates as mimics for multivalent presentation of carbohydrates" Organic letters 6;5(3):pp. 243-246. (2003).
International Preliminary Report on Patentability issued in PCT/IL2015/050562, dated Dec. 6, 2016.
Alsberg, et al., "Cell-Interactive Alginate Hydrogels for Bone Tissue Engineering", J Dent Res 80 (11), 2001, 2025-2029.
Assoian, et al., "Growth control by intracellular tension and extracellular stiffness", Trends Cell Biol 18(7), 2008, 347-352.
Benediktsdóttir, et al., "Regioselective fluorescent labeling of N,N,N-trimethyl chitosan via oxime formation", Carbohydrate Polymers 90(3), 2012, 1273-1280.
Bosker, et al., "Synthesis and Interfacial Behavior of Polystyrene-Polysaccharide Diblock Copolymers", Macromolecules 36 (6), 2003, 1982-1987.
Bottazzi, et al., "Regulation of p21cip1 Expression by Growth Factors and the Extracellular Matrix Reveals a Role for Transient ERK Activity in G1 Phase", J. Cell Biol. 146, 1999, 1255-1264.
Dirksen, et al., "Nucleophilic catalysis of oxime ligation.", Angew. Chem. Int. Ed. 45, 2006, 7581-7584.
Dirksen, et al., "Rapid Oxime and Hydrazone Ligations with Aromatic Aldehydes for Biomolecular Labeling", Bioconjugate Chem. 19, 2008, 2543-2548.
Draget, et al., "Alginic acid gels: the effect of alginate chemical composition and molecular weight", Carbohydr. Polym. 25, 1994, 31-38.
Freeman, et al., "The effect of sulfation of alginate hydrogels on the specific binding and controlled release of heparin-binding proteins.", Biomaterials 29, 2008, 3260-3568.
Guerry, et al., "Aniline-Catalyzed Reductive Amination as a Powerful Method for the Preparation of Reducing End-"Clickable" Chitooligosaccharides", Bioconjugate Chem. 24, 2013, 544-549.
Mima, et al., "Highly deacetylated chitosan and its properties", J. Appl. Polym. Sci. 28, 1983, 1909-1917.
Mizrahy, et al., "Polysaccharides as building blocks for nanotherapeutics", Chem. Soc. Rev. 41, 2012, 2623-2640.
Novoa-Carballal, et al., "Synthesis of polysaccharide-b-PEG block copolymers by oxime click", Chem. Commun. 48, 2012, 3781-3783.

(Continued)

*Primary Examiner* — Thomas S Heard
(74) *Attorney, Agent, or Firm* — Mark S. Cohen; Pearl Cohen; Zedek Latzer Baratz LLP

(57) ABSTRACT

The present invention relates to site-selective modification of polysaccharides at their reducing end by conjugation with a single aminoxy-Regioselective Addressable Functionalized Template (RAFT) peptide.

15 Claims, 21 Drawing Sheets

Specification includes a Sequence Listing.

(56) References Cited

OTHER PUBLICATIONS

Raemdonck, et al., "Polysaccharide-based nucleic acid nanoformulations", Adv. Drug Deliv. Rev. 65, 2013, 1123-1147.
Rashidian, et al., "A Highly Efficient Catalyst for Oxime Ligation and HydrazoneOxime Exchange Suitable for Bioconjugation", Bioconjugate Chem. 24, 2013, 333-342.
Re'Em, et al., "The effect of immobilized RGD peptide in macroporous alginate scaffolds on TGFbeta1-induced chondrogenesis of human mesenchymal stem cells.", Biomaterials 31, 2010, 6746-6755.
Roovers, et al., "Integrating the MAP Kinase Signal Into the G1 Phase Cell Cycle Machinery", Bioessays 22, 2000, 818-826.
Ruoslahti, "RGD and other recognition sequences for integrins.", Annu. Rev. Cell Dev. Biol. 12, 1996, 697-715.
Sapir et al., "Integration of Multiple Cell-Matrix Interactions Into Alginate Scaffolds for Promoting Cardiac Tissue Regeneration", Biomaterials 32, 2011, 1838-1847.
Schatz, et al., "Polysaccharide-Containing Block Copolymers: Synthesis, Properties and Applications of an Emerging Family of Glycoconjugates", Macromol. Rapid Commun. 31, 2010, 1664-1684.
Shachar, et al., "The effect of immobilized RGD peptide in alginate scaffolds on cardiac tissue engineering", Acta Biomater. 7, 2011, 152-162.
Styslinger, et al., "Site-Selective Glycosylation of Hemoglobin with Variable Molecular Weight Oligosaccharides: A Potential Alternative to PEGylation", J. Am. Chem. Soc. 134, 2012, 7507-7515.
Wendeler, et al., "Enhanced Catalysis of Oxime-Based Bioconjugations by Substituted Anilines", Bioconjugate Chem. 25, 2014, 93-101.
Zhang, et al., "Intracellular pH-Sensitive PEG-block-Acetalated-Dextrans as Efficient Drug Delivery Platforms", ACS Appl. Mater. Interfaces 5, 2013, 10760-10766.

SEQUENCE LISTING

<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: synthetic

<400> SEQUENCE: 1

Gly Gly Gly Gly Arg Gly Asp Tyr
1               5

<210> SEQ ID NO 2
<211> LENGTH: 16
<212> TYPE: PRT
<213> ORGANISM: Artificial Sequence
<220> FEATURE:
<223> OTHER INFORMATION: synthetic

<400> SEQUENCE: 2

Gly Gly Gly Lys Thr Ala Met Arg Ala Gly Gly Gly Arg Gly Asp Tyr
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: synthetic

<400> SEQUENCE: 3

Gly Gly Gly Gly Arg Gly Asp Tyr Lys Phe Ile Thr Cys
1               5                   10

```
<210> SEQ ID NO 4
<211> LENGTH: 14
<212> TYPE: PRT
<213> ORGANISM: Artificial Sequence
<220> FEATURE:
<223> OTHER INFORMATION: synthetic

<400> SEQUENCE: 4

Gly Gly Gly Gly Ser Pro Pro Arg Arg Ala Arg Val Thr Tyr
1               5                   10

<210> SEQ ID NO 5
<211> LENGTH: 14
<212> TYPE: PRT
<213> ORGANISM: Artificial Sequence
<220> FEATURE:
<223> OTHER INFORMATION: synthetic

<400> SEQUENCE: 5

Gly Gly Gly Gly Ser Pro Pro Leu Leu Ala Leu Val Thr Tyr
1               5                   10

<210> SEQ ID NO 6
<211> LENGTH: 15
<212> TYPE: PRT
<213> ORGANISM: Artificial Sequence
<220> FEATURE:
<223> OTHER INFORMATION: synthetic

<400> SEQUENCE: 6

Gly Gly Gly Gly Ser Pro Pro Arg Arg Ala Arg Val Thr Tyr Lys
1               5                   10                  15
```

SITE-SELECTIVE MODIFICATION OF POLYSACCHARIDES AND APPLICATIONS THEREOF

CROSS-REFERENCE TO RELATED APPLICATIONS

This application is a National Phase application of PCT Application No. PCT/IL2015/050562, filed Jun. 1, 2015, which published as WO/2015/186127 on Dec. 10, 2015, claiming benefit of priority from U.S. Patent Provisional Application Ser. No. 62/006,307, filed Jun. 2, 2014.

FIELD OF THE INVENTION

The present invention is in the field of biomaterials and, in particular, relates to site-selective modification of polysaccharides at their reducing end.

BACKGROUND OF THE INVENTION

Polysaccharides are ubiquitous polymers in nature featuring highly complex molecular structures. In recent years, polysaccharides have emerged as important functional materials because of their versatile and unique properties such as biocompatibility, biodegradability and availability of reactive sites for chemical modifications to optimize their properties.

Polysaccharides are naturally occurring polymers that are composed of monosaccharides, linked through glycosidic bonds and are found in a large variety of natural resources such as microbes, plants and animal realms. Due to their wide range of molecular weights and different chemical compositions, polysaccharides exhibit diverse physiological, chemical and biological properties. Moreover, with other unique features such as low toxicity, biocompatibility, biodegradability and multivalent binding ability, polysaccharides become attractive biomaterials in the biomedical field (Mizrahy, 2012; Raemdonck, 2013).

The presence of various functional groups in polysaccharides allows their modifications and fine-tuning their properties for biomaterial applications in tissue engineering and regenerative medicine. Consequently, different methods have been developed for the modification of polysaccharides using their lateral functional groups (e.g. —OH, —COOH) to perform etherification, esterification, amidation, sulfation, free radical initiated co-polymerization and reductive amination.

The overwhelming majority of the methods to modify polysaccharides employ random chemical modifications, which in many cases improve certain properties while compromising others. On the other hand, the employed methods for selective modifications often require excess of coupling partners, long reaction times and are limited in their scope and wide applicability.

In addition, most of these methods deal with: 1) harsh reaction conditions to which some polysaccharides cannot tolerate, 2) pre-modification of the parent polysaccharide to install the requested reactive functional groups along the backbone, 3) non-selective modifications across the chain, which often change the structure of the resultant polymers and could significantly affect their physical and biological properties. For example, alginate hydrogels are widely used in tissue engineering as the ionically cross-linked hydrogel to maintain cell viability and function during the mild gelling process. To improve the properties of these hydrogels, alginate chains are modified, for example, with cell adhesion peptides such as arginine-glycine-aspartate (RGD), by employing carbodiimide chemistry to randomly modify the carboxylic groups in alginate monomers (Alsberg, 2001; Re'em, 2010; Shachar, 2011). As a result, this might reduce the availability of the carboxylic acid groups for calcium crosslinking, thus affecting the extent of alginate gelation and leading to relatively poor mechanical properties of the hydrogel.

Alginate is a polysaccharide derived from brown seaweed. It is an anionic polysaccharide composed of uronic acids (guluronic (G) and mannuronic (M) acids) that undergoes gelation in the presence of bivalent cations, such as $Ca^{2+}$ and $Ba^{2+}$. In the pharmaceutical/medicinal fields, it is used successfully as encapsulation material, mostly for cells (bacterial, plant and mammalian cells).

In order to overcome these difficulties, end group chemistry has been developed for the selective modification of polysaccharides, where the terminal carbonyl group undergoes modification without affecting the rest of the functional groups. This has attracted much attention because it preserves the inherent physical properties of the natural polysaccharide as well as obviating the need for pre-modifications (Schatz, 2010). Generally, this approach involves condensations via imine (Bosker, 2003; Guerry, 2013; Zhang, 2013) and oxime-forming reactions carried out on the terminal aldehyde (in equilibrium with hemiacetal).

Oxime chemistry has emerged as a powerful tool for the chemoselective conjugation of polysaccharides, owing to the high reactivity of the aminoxy functionality with the aldehyde group. In addition, this reaction can be performed in aqueous medium, under mild acidic conditions and the resulting oxime bond is stable at physiological conditions (Benediktsdottir, 2012; Novoa-Carballal, 2012; Styslinger, 2012). However, the overwhelming majority of the reports employing such a chemistry often use excess coupling partners, prolonged reaction times (>24 h) and low pH (WO 2003/024984), to which some polysaccharides may be sensitive as is the case with alginate, which is known to form gels at pH≤3 (Draget, 1994).

The urgent need of efficient bioconjugation chemistry to modify macromolecules (e.g. proteins) prompted the development of aniline and its derivatives as nucleophilic catalysts for rapid oxime formation. These catalysts enable the generation of a more populated protonated aniline Schiff base from the less populated carbonyl group and subsequent transimination with nucleophilic oxyamine (Dirksen, 2008; Dirksen, 2006; Rashidian, 2013; Wendeler, 2014).

DETAILED DESCRIPTION OF THE INVENTION

Modification of polysaccharides is important in order to optimize their properties. The availability of reactive sites in the polysaccharide molecules for chemical modifications plays a major role in the modification methods.

The overwhelming majority of the methods to modify polysaccharides employ random chemical modifications, which in many cases improve certain properties while compromising others. On the other hand, the employed methods for selective modifications often require excess of coupling partners, long reaction times and are limited in their scope and wide applicability.

To circumvent these drawbacks, a method was developed according to the present invention based on aniline catalyzed oxime formation for selective modification of a variety of polysaccharides through their reducing end. For this purpose, functionalized peptides bearing an oxime group at their amino end were conjugated to a polysaccharide molecule under aniline catalysis, leading to modified polysaccharides bearing at their reducing end an aminoxy-functionalized peptide molecule.

Figure 1:
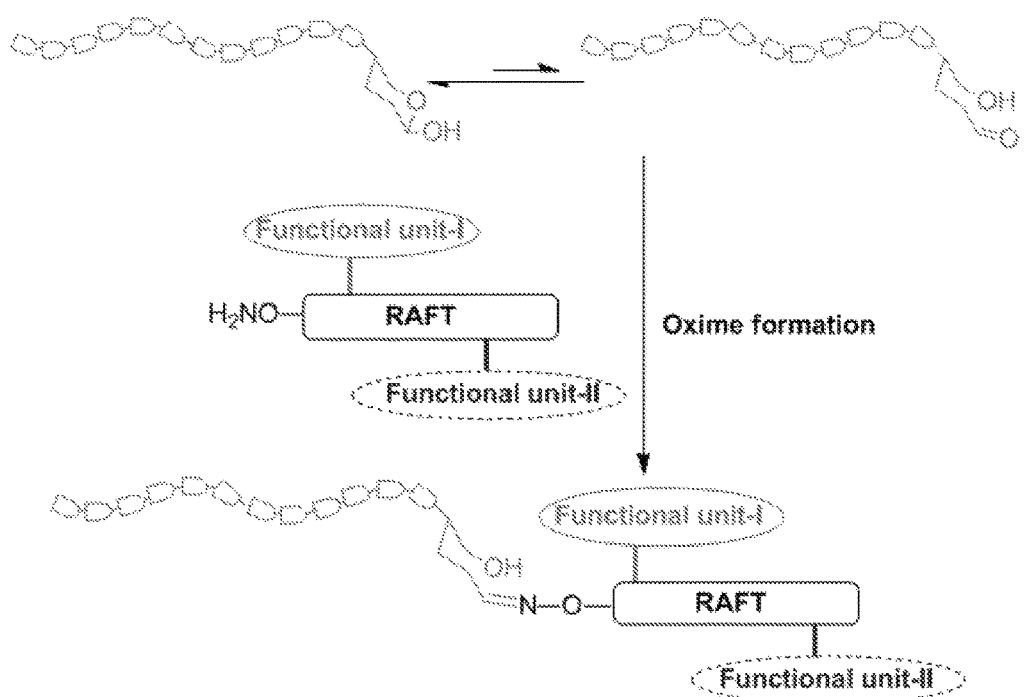
FIG. 1 is a schematic representation of end group oxime conjugation with RAFT template carrying multiple functional units.

The "functionalized peptide" is in fact a template platform to which one or more functional units can be linked as shown in FIG. 1 and is identified herein as "Regioselective Addressable Functionalized Template (RAFT) peptide". The terms "functionalized peptide" and "RAFT peptide" are sometimes used interchangeably herein in the specification and claims. The term "functional unit" means any radical or residue bound to the RAFT peptide and either exhibiting a biological activity, e.g. biomolecules such as peptides, oligosaccharides, and the like, or the functional unit is a label such as a dye, biotin, or a radioactive label.

Accordingly, the present invention provides a modified polysaccharide selectively modified at its reducing end by conjugation with a single aminoxy-Regioselective Addressable Functionalized Template (RAFT) peptide.

The polysaccharide may be in its natural form or a derivative thereof. Examples of polysaccharides and derivatives thereof that can be used in the present invention include, without being limited to, chitosan, dextran, heparin, heparan sulfate, keratin sulfate, pectin, starch, hyaluronic acid, sulfated hyaluronan (hyaluronan sulfate), alginate, alginate sulfate, and chondroitin sulfate.

In certain embodiments, the polysaccharide is dextran, chitosan, hyaluronic acid and alginate. In certain embodiments, the polysaccharide is a polysaccharide derivative including alginate sulfate and hyaluronan sulfate.

As mentioned above, the term "RAFT" peptide refers to a template platform that can be used as a suitable scaffold to independently and separately bind functional units. In certain embodiments, the RAFT peptide is linear and may contain at least two, three, four, five, six, seven, eight, nine, fourteen, fifteen and more, amino acid residues. In other embodiments, the RAFT peptide is cyclic and may contain at least four amino acids. In certain embodiments, the cyclic peptide is a cyclic decapeptide. In specific embodiments, the RAFT peptide is labeled.

In certain embodiments, the RAFT peptide is a biologically active peptide, which may also be labeled, for example, with: a dye, biotin, nuclear localization signal (NLS) or any other label known in the art. In certain embodiments, such a label is linked to a lysine residue of the RAFT peptide.

Examples of biologically active peptides include, without being limited to, pro-apoptotic, anti-apoptotic, cell proliferation-promoting, and a cell adhesion promoting peptide. In certain embodiments, the peptide may have more than one biological activity, for example, adhesion of cells to a cell adhesion promoting peptide which also carries an RGD sequence, may lead in certain cells to cell proliferation and anti-apoptosis.

In certain embodiments, the cell adhesion promoting peptide adheres to cells via integrins and comprises the sequence RGD. Examples of RGD peptides suitable for use according to the invention include, without being limited to: GGGGRGDY (SEQ ID NO: 1), hereinafter in the Examples referred to as Peptide 1, or said RGD peptide is labeled and has the sequence GGGK(TAMRA)GGGRGDY (SEQ ID NO: 2), hereinafter in the Examples referred to as Peptide 3, wherein TAMRA is the fluorophore label 5-carboxytetramethylrhodamine, or GGGGRGDYK-(FITC) (SEQ ID NO: 3).

In certain embodiments, the cell adhesion promoting peptide adheres to cells via integrin-independent mechanism such as heparin-binding peptides (HBP). Examples of HBP suitable for use according to the invention include, without being limited to: GGGGSPPRRARVTY (SEQ ID NO: 4); GGGGSPPLLALVTY (SEQ ID NO: 5); and GGGGSP-PRRARVTYK-(Rhodamine B) (SEQ ID NO: 6).

In certain embodiments, the RAFT peptide is not a biologically active peptide and carries a label, for example, a label for imaging such as a fluorescent dye.

In certain embodiments, said modified polysaccharide of the invention is dextran modified by a cell adhesion promoting RGD peptide. In a specific embodiment, said modified dextran has the structure of dextran-GGGGRGDY, wherein the reducing end of dextran is linked to the amino end of the RGD peptide via an aminoxy radical.

In certain embodiments, said modified polysaccharide of the invention is chitosan modified by a cell adhesion promoting RGD peptide. In a specific embodiment, said modified chitosan has the structure of chitosan-GGGGRGDY, wherein the reducing end of chitosan is linked to the amino end of the RGD peptide via an aminoxy radical.

In certain embodiments, said modified polysaccharide of the invention is hyaluronic acid (hyaluronan) modified by a cell adhesion promoting RGD peptide. In a specific embodiment, said modified hyaluronic acid has the structure of hyaluronic acid-GGGGRGDY, wherein the reducing end of hyaluronic acid is linked to the amino end of the RGD peptide via an aminoxy radical.

In certain embodiments, said modified polysaccharide of the invention is alginate sulfate modified by a cell adhesion promoting RGD peptide. In a specific embodiment, said modified alginate sulfate has the structure of alginate sulfate-GGGGRGDY, wherein the reducing end of alginate sulfate is linked to the amino end of the RGD peptide via an aminoxy radical.

In certain embodiments, said modified polysaccharide of the invention is alginate modified by a cell adhesion promoting RGD peptide. In a specific embodiment, said modified alginate has the structure of alginate-GGGK(TAMRA)GGGRGDY, wherein the reducing end of alginate is linked to the amino end of the RGD peptide via an aminoxy radical and the conjugate is labeled with the dye TAMRA.

In certain embodiments, said modified polysaccharide of the invention is hyaluronan sulfate modified by a cell adhesion promoting RGD peptide, NLS or TAMRA-NLS. In a specific embodiment, the reducing end of hyaluronan sulfate is linked to the amino end of the RGD peptide or NLS via an aminoxy radical and the conjugate may be labeled with the dye TAMRA. In yet another specific embodiment, a PEG moiety is present in between the hyaluronan sulfate and NLS.

In certain embodiments, said modified polysaccharide of the invention is alginate modified by a RGD-HBP peptide, having the structure of YDGRGGGG-(K-ONH$_2$)-GGGGSPPRRARVTY-ONH$_2$, wherein the reducing end of alginate is linked to the amino end of this RGD-HBP peptide via an aminoxy radical.

The present invention further relates to a process for the preparation of modified polysaccharides according to the invention comprising conjugation of a polysaccharide with an aminoxy-functionalized peptide in the presence of aniline.

Notably, it has been found in accordance with the present invention that for efficient oxime formation, different conditions are required depending on the molecular weight and composition of the specific polysaccharide. The present invention further shows how this strategy can be applied to improve the physical and functional properties of various modified polysaccharides, especially alginate hydrogels, which are widely used in tissue engineering and regenerative medicine applications As demonstrated herein in the Examples, a highly efficient strategy for the selective and rapid conjugation of various polysaccharides with aminoxy-functionalized peptides according to the present invention was achieved. It was found that the size and the chemical composition of the polysaccharides have a remarkable effect on the efficiency of the reactions. For example, highly negatively charged polysaccharides such as alginate sulfate did not form the desired oxime conjugate unless arginine was added, which presumably interfere with the nonproductive ionic complexation between the reaction components.

The present invention further demonstrates the advantages of performing selective modifications on functional polysaccharide, by comparing physical and biofunctional properties of the different conjugates in a hydrogel form with the randomly modified ones. Although the viscoelastic properties of the alginate conjugates synthesized by either method were comparable, the selectively modified conjugate of the invention formed a significantly more stable hydrogel that exhibited strong cell adhesive properties and provided a highly cooperative microenvironment for gene induction associated with cell proliferation.

The results provided herein on the site-selective modification of polysaccharides by oxime conjugation catalyzed by aniline has significant importance in constructing potentially useful functional materials such as matrices for tissue engineering and regenerative medicine applications, as well as hydrogels and nano-carriers for targeted drug delivery.

It must be noted that, as used in this specification and the appended claims, the singular forms "a", "an" and "the" include plural referents unless the content clearly dictates otherwise.

The invention will now be further described and illustrated in the following non-limiting examples.

EXAMPLES

1. Experimental 1.1 General

Solid phase peptide synthesis (SPPS) was carried out manually in syringes, equipped with teflon filters, purchased from Torviq. If it is not differently described, all reactions were carried out at room temperature. Analytical HPLC was performed on a Thermo instrument (Spectra System P4000) using an analytical column (Jupiter 5 micron, C18 300 Å 150×4.6 mm) at a flow rate of 1.2 mL/min. Preparative HPLC was performed on a Waters instrument using a preparative column (Jupiter 10 micron, C18 300 Å, 250× 22.4 mm) at a flow rate of 15 mL/min. Buffer A: 0.1% trifluoroacetic acid (TFA) in water; Buffer B: 0.1% TFA in acetonitrile. Mass spectrometry analysis was carried out using a LCQ Fleet Ion Trap (Thermo Scientific). UV spectra were recorded on a JASCO V-550 UV/Vis spectrophotometer and fluorescence spectra were recorded using a Fluorolog 3 (Jobin-Yvon) steady-state Spectrometer. NMR spectra were recorded in $D_2O$ using a Bruker AMX-400 MHz spectrometer for all samples, except for chitosan where a mixture of $D_2O$ and DCl (pH 4) was used. Chemical shifts are reported in ppm (δ units) downfield from internal 3-(trimethylsilyl)-propionic acid-d4.

1.2 Materials and Methods

Dextran (Mn ~6 kD) was purchased from Sigma-Aldrich and used after dialysis with a membrane of molecular weight cut off (MWCO) of 3 kD. Chitosan was also purchased from Sigma-Aldrich (low molecular weight) and deacetylated with sodium hydroxide treatment (Mima, 1983). Hyaluronic acid (~51 kD) was purchased from Lifecore Biomedical LLC (USA). Alginate, VLVG type with 65% guluronic acid content and molecular weight of 32 kD was purchased from NovaMatrix/FMC Biopolymers, Drammen, Norway. Alginate sulfate and hyaluronan sulfate were synthesized according to the literature report (Freeman 2008). Ultrafiltration membranes of MWCO 3 kD and 7 kD were purchased from Thermoscientific. Resins, protected amino acids and HBTU, HCTU, HATU, were purchased from Novabiochem, Aapptec Luxemborg and Chem-Impex. DMF was purchased in biotech grade.

1.3 Cell Analysis by Fluorescent Microscopy

After 24 h seeding on hydrogel films, PHK67-labeled cells were visualized under a fluorescent microscope (Olympus IX-70) equipped with DP71 digital camera (Olympus).

1.4 Statistical Analysis

Statistical analysis was performed with GraphPad Prism version 6.01 for Windows (GraphPad Software, San Diego, Calif.). All variables are expressed as mean±SEM. To test the hypothesis that changes in cell DNA content, metabolic activity, and gene expression varied over time among the experimental groups, a general linear 2-way ANOVA model was used. The model included the effects of treatment, time, and treatment-by-time interaction. The Bonferroni's correction was used to assess the significance of predefined comparisons at specific time points. $P<0.05$ was considered statistically significant.

2. Examples

Example 1

Synthesis of Peptide 1

Figure 2A:
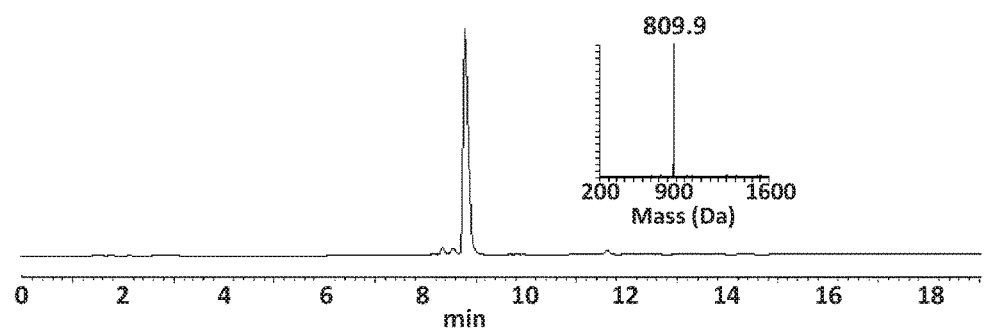
FIGS. 2A-D are graphs showing analytical HPLC traces: (A) shows analytical HPLC and mass analysis of oxime-peptide 1, H$_2$NO-GGGGRGDY, with the observed mass of 809.9 Da (calc. 809.7 Da); (B) shows analytical HPLC traces for the reaction between oxime-peptide 1 and Dextran in the absence of aniline. Peak 'a' corresponds to oxime-peptide 1 and peak 'b' corresponds to RGD-aminoxy-Dextran; (C) shows analytical HPLC traces for the reaction between oxime-peptide 1 and dextran in the presence of aniline. Peak 'a' corresponds to aniline, peak 'b' corresponds to oxime-peptide 1 and peak 'c' corresponds to the conjugated product, peptide-aminoxy-dextran; and (D) shows analytical HPLC traces of dextran-aminoxy-peptide conjugate after dialysis.
Figure 2B:
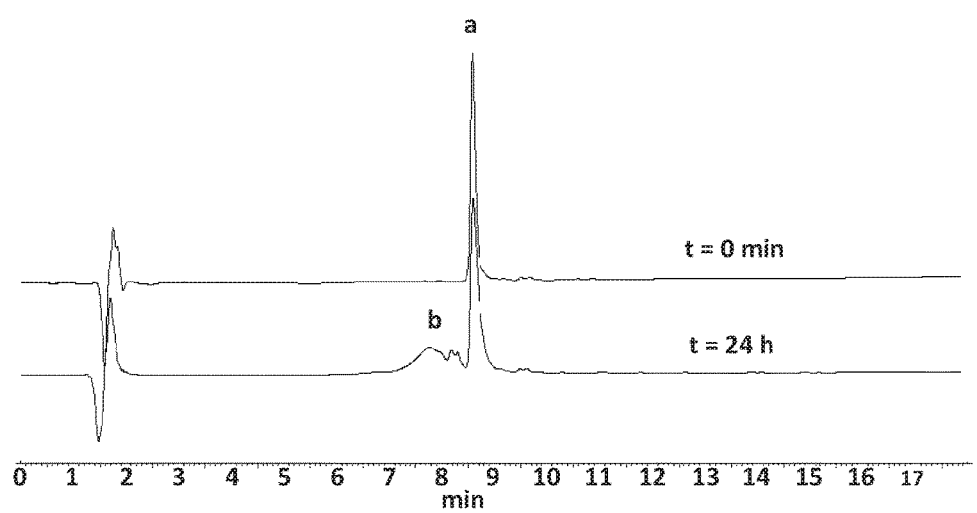
Figure 2C:
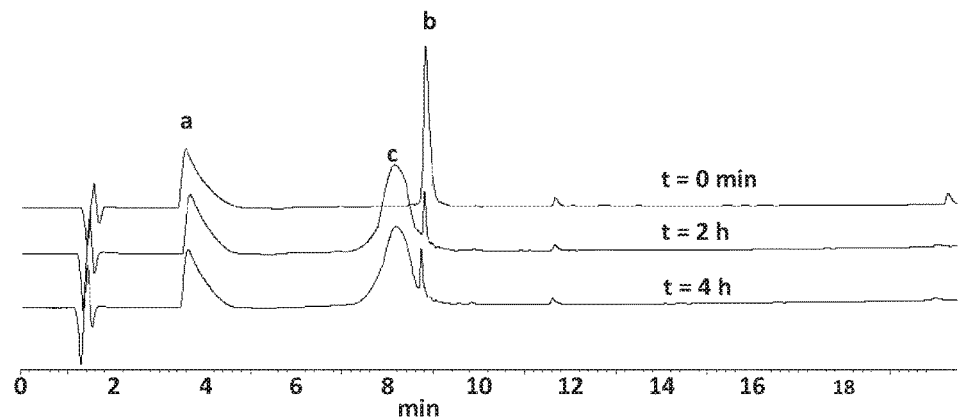
Figure 2D:
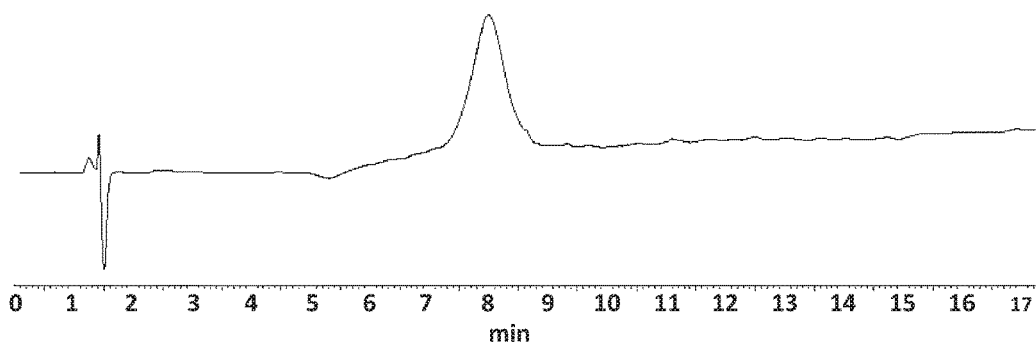

To begin examining the oxime formation at the polysaccharide-reducing end, a model peptide GGGGRGDY (SEQ ID NO: 1) was synthesized via solid phase peptide synthesis (SPPS) in which the aminoxy functionality was introduced at the N-terminus by coupling Boc-aminoxyacetic acid (Boc-Aoa). Following peptide cleavage from the resin, the resulting Aoa-GGGGRGDY peptide (peptide 1) was isolated and analyzed by HPLC and mass spectrometry. FIG. 2A shows analytical HPLC and mass analysis of oxime-peptide 1, $H_2NO$-GGGGRGDY, with the observed mass of 809.9 Da (calc. 809.7 Da); FIG. 2B shows analytical HPLC traces for the reaction between oxime-peptide 1 and Dextran in the absence of aniline. Peak 'a' corresponds to oxime-peptide 1 and peak 'b' corresponds to RGD-aminoxy-Dextran; FIG. 2C shows analytical HPLC traces for the reaction between oxime-peptide 1 and dextran in the presence of aniline. Peak 'a' corresponds to aniline, peak 'b' corresponds to oxime-peptide 1 and peak 'c' corresponds to the conjugated product, peptide-aminoxy-dextran; and FIG. 2D shows analytical HPLC traces of dextran-aminoxy-peptide conjugate after dialysis.

Example 2

Oxime Reaction Between Peptide 1 and Dextran

Dextran (50 mg) and peptide 1 (13 mg, ~2 equivalents) were thoroughly mixed in 8 mL of 6 M Gn.HCl buffer solution containing 100 mM aniline (pH 4.5) and the reaction was followed by HPLC. After completion of the reaction, the mixture was dialyzed against deionized water until complete elimination of excess of peptide 1, as observed by HPLC analysis, followed by lyophilization to obtain a white foamy material.

Figure 3A:
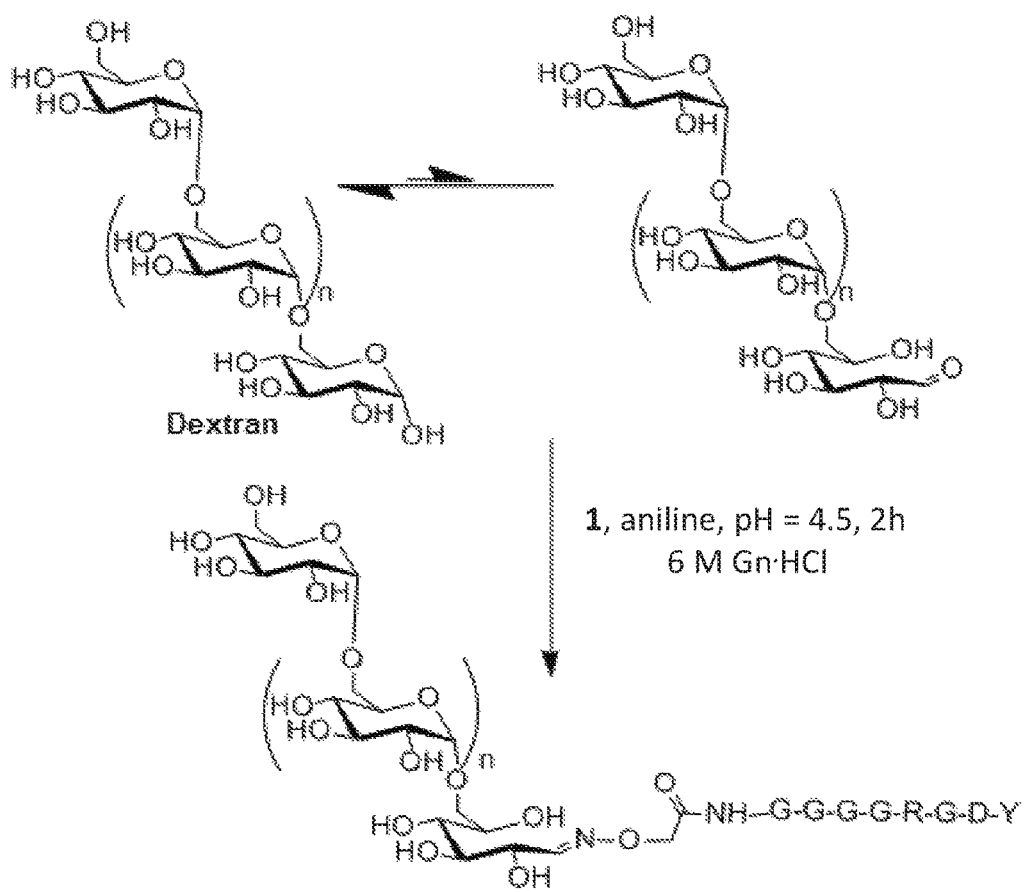
FIGS. 3A-C represent oxime conjugation reaction for dextran: (A) depicts a schematic representation of oxime conjugation reaction for dextran. (B) is a graph showing analytical HPLC traces for the reaction between oxime-peptide 1 depicted in A and dextran in presence of aniline. Peak 'a' corresponds to aniline, peak 'b' corresponds to oxime-peptide and peak 'c' corresponds to the desired conjugated product dextran-aminoxy-GGGGRGDY. (C) depicts the $^1$H NMR analysis of dextran-aminoxy-GGGGRGDY.
Figure 3B:
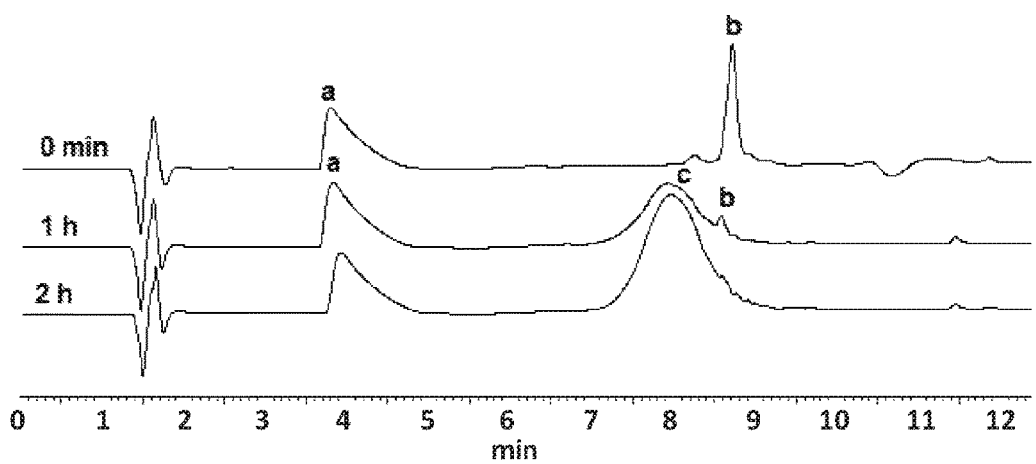

Optimization of oxime bond formation was first examined by reacting the aminoxy peptide 1 with dextran (Mn ~6 kD, Mn is the number average molecular weight) as a neutral and low molecular weight polysaccharide (FIG. 3A). In a typical reaction, equimolar quantities of the starting materials were mixed in the presence of 100 equivalents of aniline in 6 M Gn.HCl buffer, pH 4.5, where the population of the aldehyde functionality will be higher than at neutral pH. The progress of the reaction was monitored by analytical HPLC. Within 2 hours, the peak corresponding to the aminoxy peptide in the HPLC analysis vanished; suggesting complete consumption and a new peak was observed possibly due to the formation of the desired oxime conjugate (FIG. 3B).

Figure 3C:
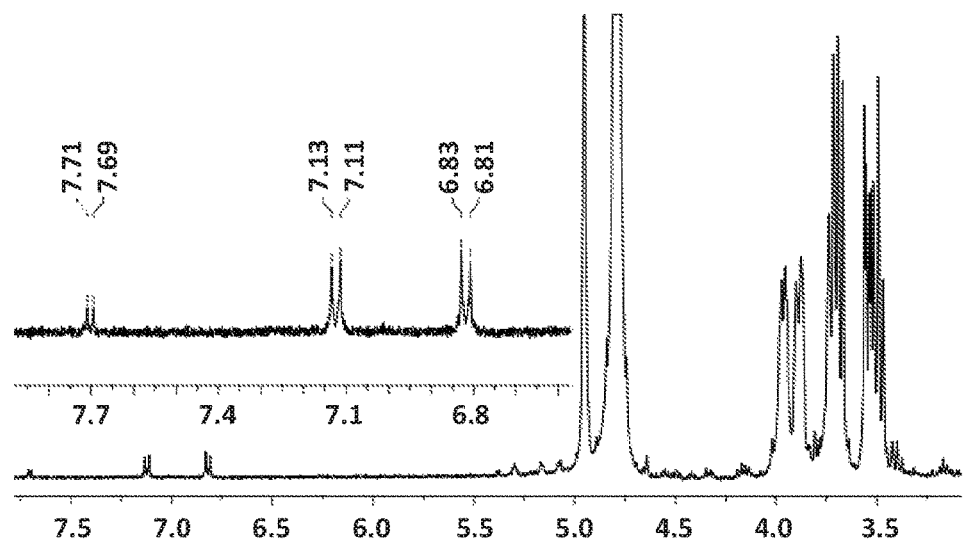

When the reaction was carried out in the absence of aniline, it was very sluggish and the majority of the starting material remained unreacted even after prolonged reaction time. This suggests a significant role of aniline in the nucleophilic catalysis and acceleration of oxime formation. When the reaction was repeated with excess peptide (2 equivalents with respect to Dextran), the HPLC peaks correspond to the starting material and product attained saturation within 4 h wherein elongation of reaction time did not improve it any further, suggesting the completion of the reaction. Subsequently, the reaction mixture was dialyzed against deionized water to remove excess of aminoxy peptide, lyophilized and the residue was analyzed by HPLC and $^1$NMR. HPLC analysis showed a single peak confirming the purity of the product after dialysis. The $^1$NMR spectrum exhibited the characteristic peak of —ON=CH— at 7.7 ppm, which indicates the presence of oxime bond between dextran and RGD, thus confirming the integrity of the expected product (FIG. 3C).

Example 3

Oxime Reaction Between Peptide 1 and Deacetylated Chitosan

Having these conditions in hand, the strategy was extended for conjugating peptide 1 to a relatively high molecular weight and positively charged deacetylated chitosan (Mn ~50 kD). Since, the deacetylated chitosan was not soluble in 6 M Gn.HCl, acetic acid (0.1 M) was added to aid its dissolution.

Deacetylated chitosan (400 mg) and peptide 1 (13 mg, ~2 equivalents) were mixed in 8 mL of 6 M Gn.HCl buffer solution containing 0.1% (v/v) acetic acid and 100 mM aniline (pH 4.5). The resulting reaction mixture was thoroughly mixed by gentle shaking. The reaction was analyzed and worked up as in the dextran example.

Figure 4A:
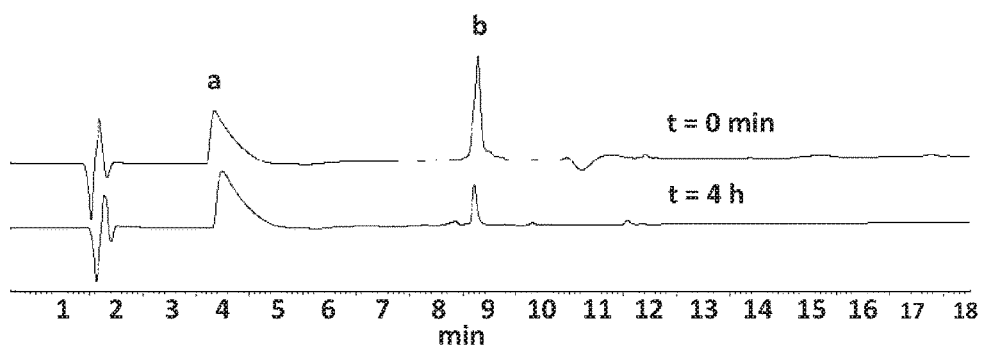
FIGS. 4A-C represent oxime conjugation reaction for deacetylated chitosan: (A) is a graph showing analytical HPLC traces for the reaction between oxime-peptide 1 and deacetylated chitosan in the presence of aniline. Peak 'a' corresponds to aniline and peak 'b' corresponds to oxime-peptide 1; (B) is a graph showing analytical HPLC traces for the reaction between oxime-peptide 1 and alginate in the presence of aniline. Peak 'a' corresponds to aniline and peak 'b' corresponds to oxime-peptide 1; and (C) depicts the $^1$H NMR of deacetylated chitosan-aminoxy-GGGGRGDY, (400 MHz, D2O, 293K).
Figure 4B:
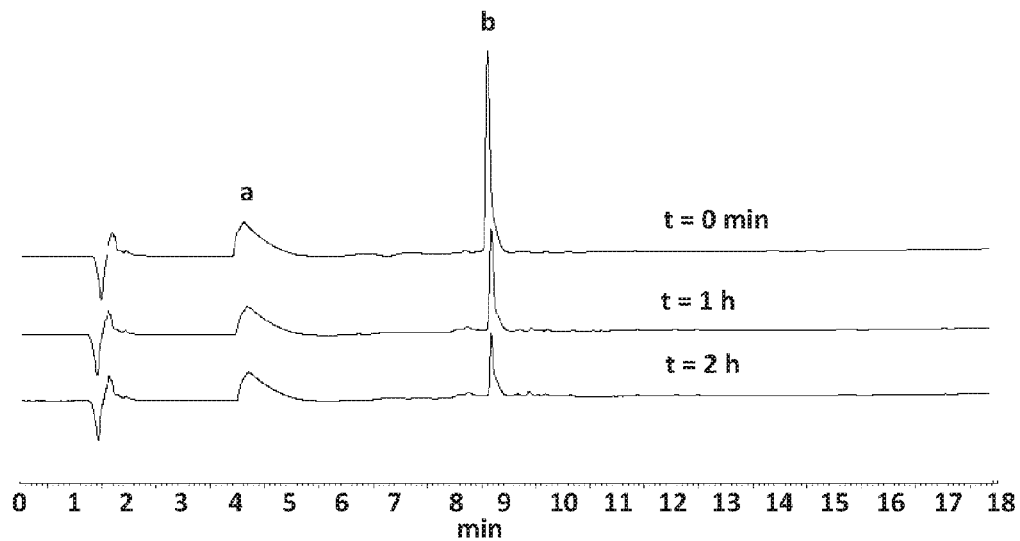
Figure 4C:
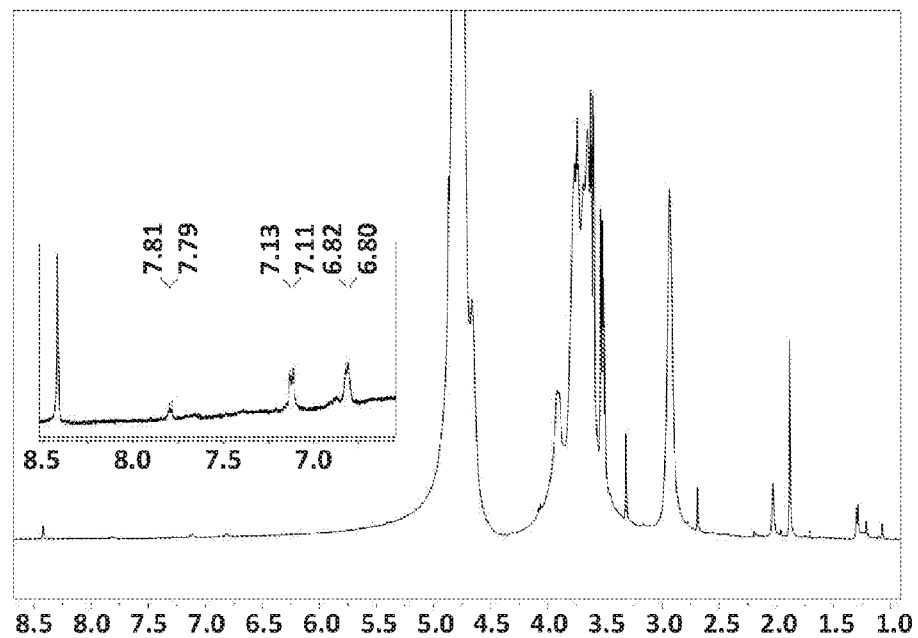

All efforts to trace the peptide conjugated deacetylated chitosan in HPLC were not successful, hence it was decided to initially monitor the reaction by following the consumption of the aminoxy peptide 1. When the reaction of peptide 1 with deacetylated chitosan (2:1 ratio) was run in the presence of aniline, the intensity of peptide 1 in HPLC diminished gradually suggesting the progress of the reaction, which reached saturation within 4 h (FIG. 4A). This was concluded as the end point of the reaction, which was followed by dialysis against deionized water and lyophilization. As expected, the $^1$HNMR spectrum of the dialyzed sample had the expected signal at 7.8 ppm of the oxime bond (FIG. 4C).

Example 4

Oxime Reaction Between Peptide 1 and Hyaluronic Acid

Next, the conjugation reaction was examined on hyaluronic acid (Mn ~51 kD), a negatively charged and highly water-soluble polysaccharide comprised of glucosamine and mannuronic acid.

Hyaluronic acid (200 mg) and aminoxy peptide (13 mg, ~2 equivalents) were mixed in citrate and acetonitrile (1:1) buffer solution mixture containing 100 mM aniline (pH 4.5). The resulting reaction mixture was thoroughly mixed by gentle shaking. The reaction was analyzed and worked up as in the dextran example.

Figure 5A:
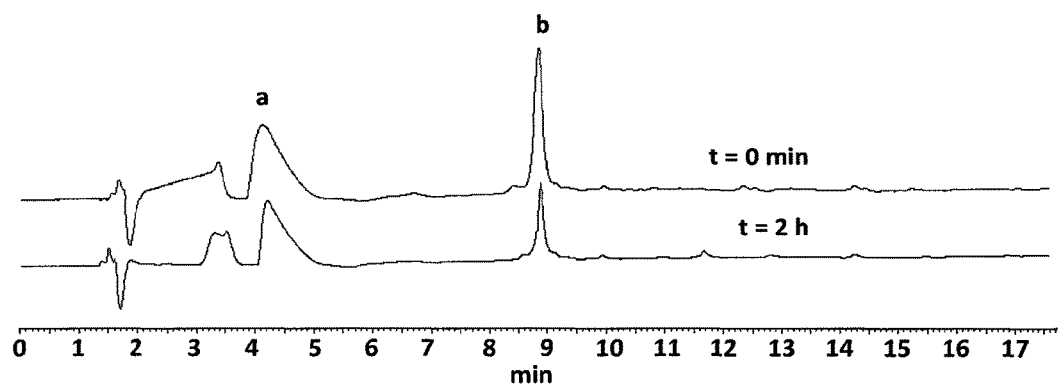
FIG. 5A-B represent oxime conjugation reaction for hyaluronic acid: (A) is a graph showing analytical HPLC traces for the reaction between aminoxy peptide 1 and hyaluronic acid in presence of aniline. Peak 'a' corresponds to aniline and peak 'b' corresponds to peptide 1; (B) depicts the $^1$H NMR of hyaluronic acid-aminoxy-GGGGRGDY, (400 MHz, D2O, 293K).
Figure 5B:
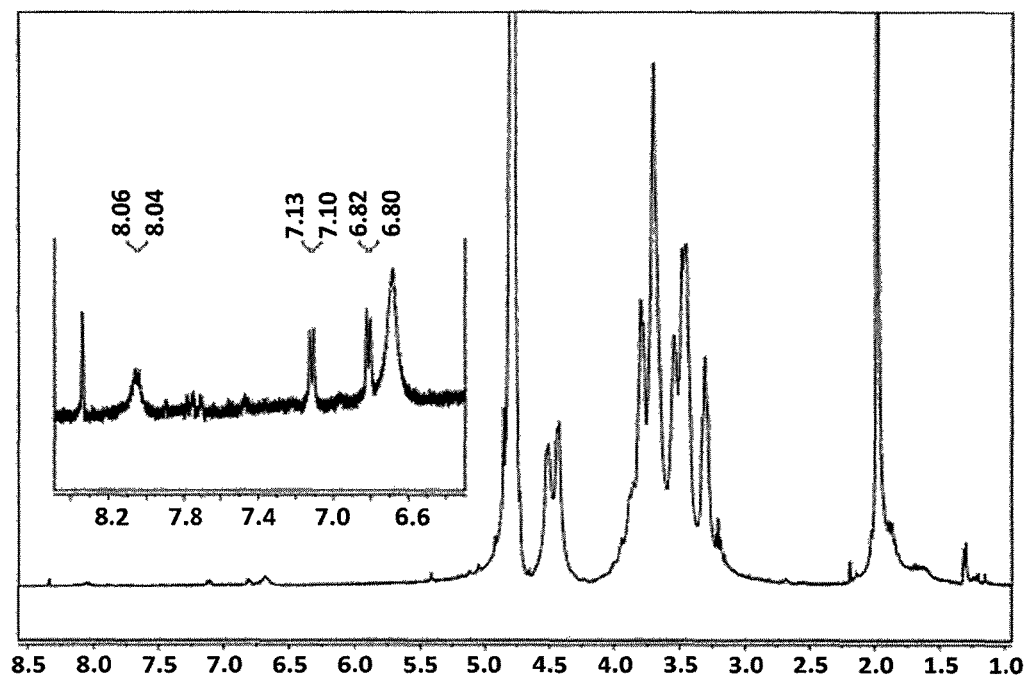

A reaction between peptide 1 and hyaluronic acid was attempted under similar conditions as described above in Example 3. However, HPLC analysis indicated no progress of the reaction despite the fact that both the peptide and the polysaccharides were highly soluble in the Gn.HCl buffer. This prompted to screening the reaction in various buffers, finding that a mixture of citrate buffer (pH 4.5) and acetonitrile (1:1) allowed a smooth reaction (FIG. 5A). The difference in the reactivity of the hyaluronic acid in different buffers could be a result of various polysaccharide conformations, which could influence the availability of the reducing end for oxime formation. The resulting conjugate, after dialysis and lyophilization, was analyzed by $^1$NMR spectroscopy supporting the formation of the desired conjugate (FIG. 5B).

Example 5

Oxime Reaction Between Peptide 1 and Alginate Sulfate

To test the generality of the developed strategy on highly negatively charged polysaccharides, alginate sulfate (Freeman, 2008) was employed as a substrate in the oxime formation reaction.

Alginate sulfate (200 mg) and arginine (300 mg) were thoroughly mixed in 8 mL of 6 M Gn.HCl buffer solution containing 100 mM aniline and the pH of the resulting reaction mixture was adjusted to 4.5. Then peptide 1 (13 mg, ~2 equivalents) was added to this reaction mixture and the progress of the reaction was followed by HPLC. The reaction was analyzed and worked up as in the dextran example.

Figure 6:
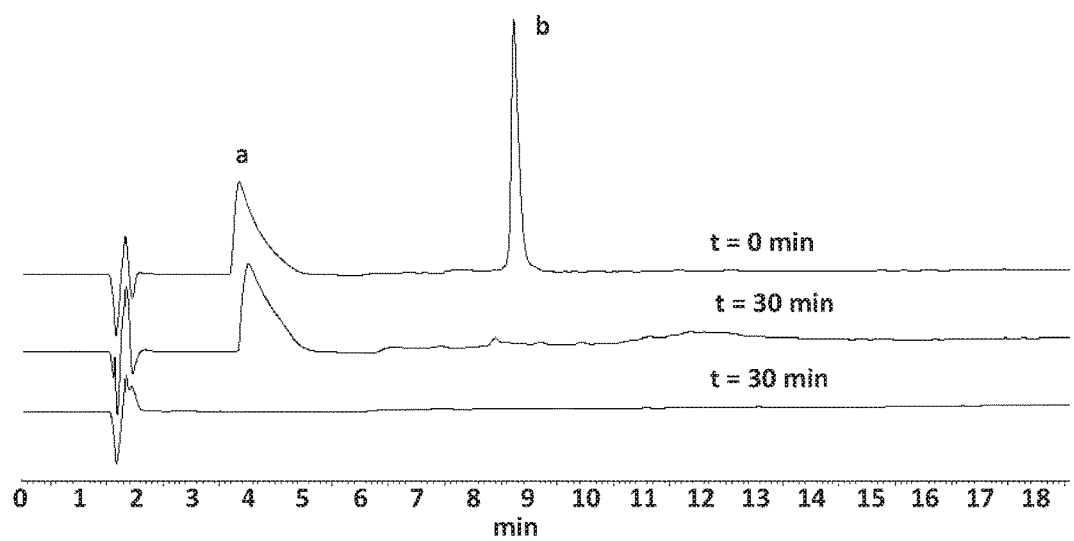
FIG. 6 depicts analytical HPLC traces for the reaction between aminoxy peptide 1 and alginate sulfate with and without aniline catalyst. Peak 'a' corresponds to aniline and peak 'b' corresponds to peptide 1.
Figure 7:
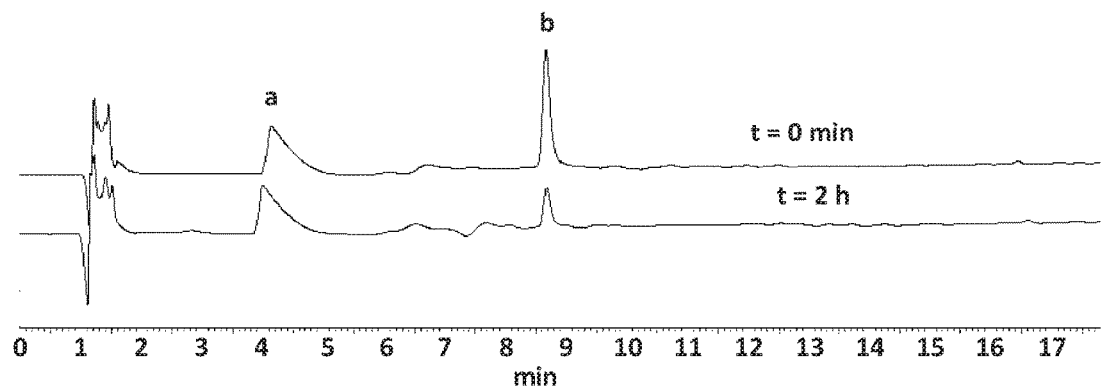
FIG. 7 depicts analytical HPLC traces for the reaction between aminoxy peptide 1 and alginate sulfate in the presence of excess of arginine and aniline. Peak 'a' corresponds to aniline and peak 'b' corresponds to peptide 1.

When alginate sulfate was mixed with 2 equivalents of peptide 1, a complete consumption of aminoxy peptide was observed (FIG. 6) within 30 min, regardless of the presence or absence of aniline. This was unexpected since previous experiments indicated that this reaction is extremely slow in the absence of aniline. This led to the speculation that peptide 1, instead of reacting via oxime formation, underwent ionic complexation, presumably via its arginine side chain, with the highly negatively charged alginate sulfate. To further test this speculation, another experiment was carried out wherein the same peptide sequence lacking the aminoxy functionality (peptide 2) was prepared and treated with the alginate sulfate under similar conditions. Even in this case a rapid and complete consumption of the peptide was observed. To interfere with the complexation of the peptide with alginate sulfate, it was treated with excess of arginine to generate favorable complexation with the positively charged guanidinium groups. To this mixture, aniline and aminoxy peptide 1 were added and the pH was adjusted to 4.5. After 2 h, rapid consumption of the starting material was observed (FIG. 7). However, under these conditions peptide 2 remained intact, further supporting the specificity of the reaction with aminoxy peptide and the role of arginine to inhibit nonproductive complex formation.

Example 6

Synthesis of Peptide 3

Figure 8:
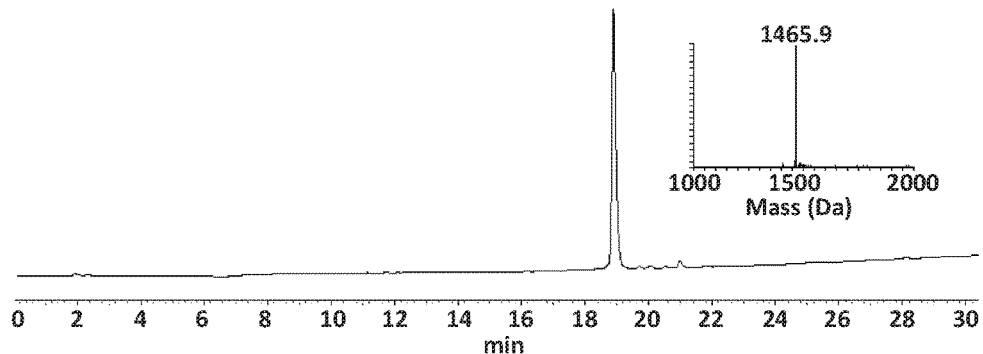
FIG. 8 depicts HPLC and mass analysis of peptide 3, H$_2$NO-GGGK(TAMRA)GGGRGDY, with the observed mass of 1465.9 Da (calc. 1466 Da).

In order to examine the efficiency of the oxime reaction with fluorescence analysis and further to open future opportunities in tracking polysaccharides in cellular context, the complexity of the RAFT template was increased by including a fluorophore thereto. For this, 5-carboxytetramethylrhodamine (TAMRA) was linked to the Lys side chain during SPPS to obtain Aoa-GGGK(TAMRA)-GGGRGDY (peptide 3), which was purified by HPLC and characterized by mass spectrometry (FIG. 8).

Example 7

Oxime Reaction Between Peptide 1 and Alginate

Alginate (250 mg) and peptide 1 (13 mg, ~2 equivalents) were thoroughly mixed in 8 mL of 6 M Gn.HCl buffer solution containing 100 mM aniline (pH 4.5) and the reaction was followed by HPLC. After completion of the reaction, the mixture was dialyzed against deionized water until complete elimination of excess of peptide 1, as observed by HPLC analysis, followed by lyophilization to obtain a white foamy material (FIG. 4B).

Example 8

Oxime Reaction Between Peptide 3 and Alginate

Figure 9A:
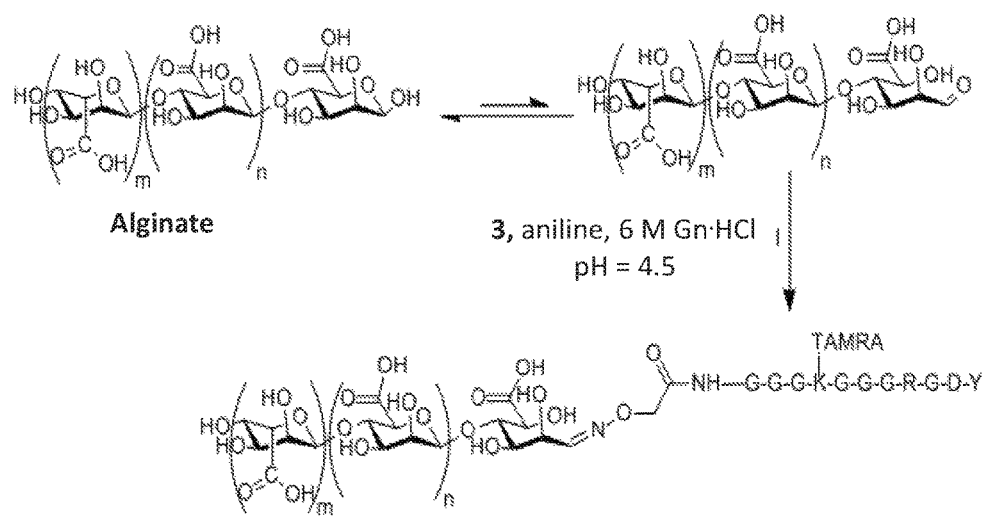
FIGS. 9A-D represent oxime conjugation reaction for alginate and peptide 3: (A) is a schematic representation of oxime formation reaction between alginate and peptide 3; (B) shows an HPLC analysis of oxime formation reaction between alginate and peptide 3; (C) shows a UV-visible analysis of peptide 3 (1 mg/100 ml of H$_2$O) and conjugate 4 (1 mg/10 ml of H$_2$O); and (D) shows a fluorescence analysis of peptide 3 (1 mg/100 ml of H$_2$O) and conjugate 4 (1 mg/10 ml of H$_2$O).
Figure 9B:
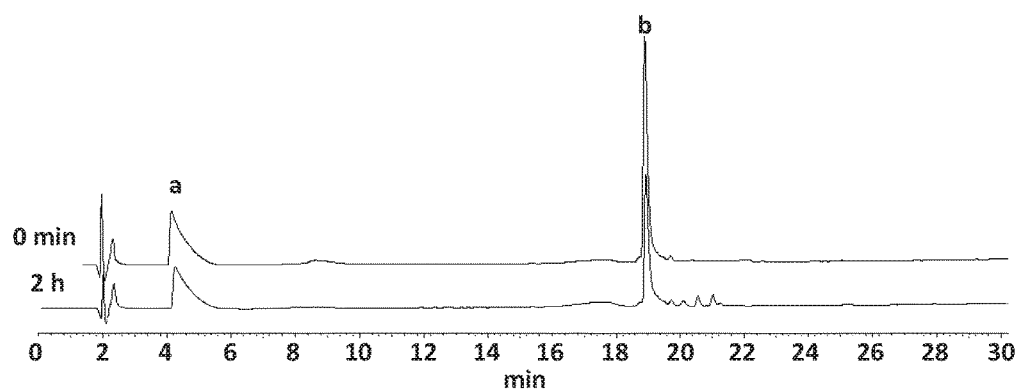
Figure 9C:
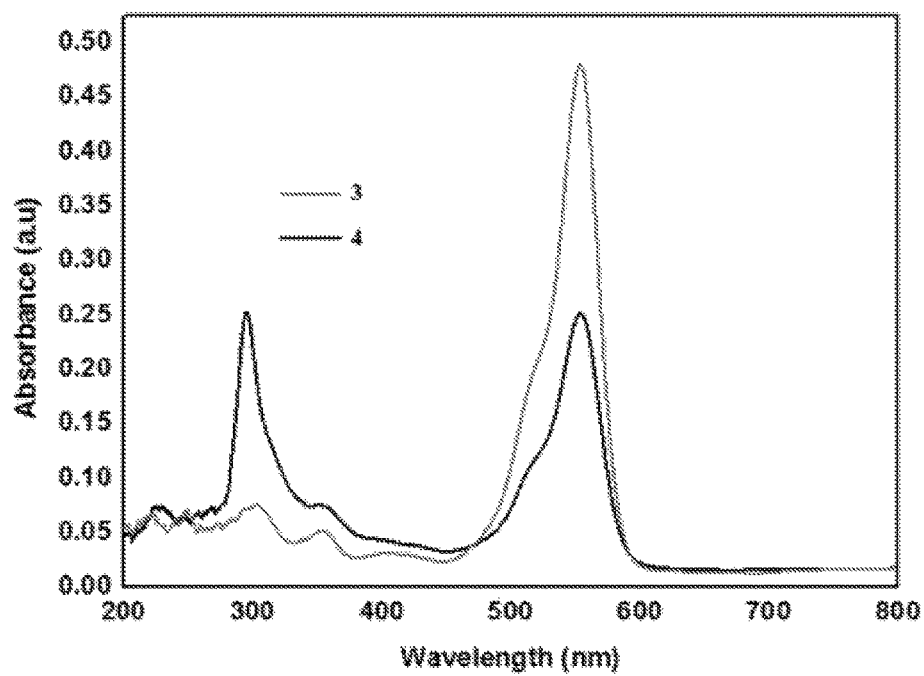
Figure 9D:
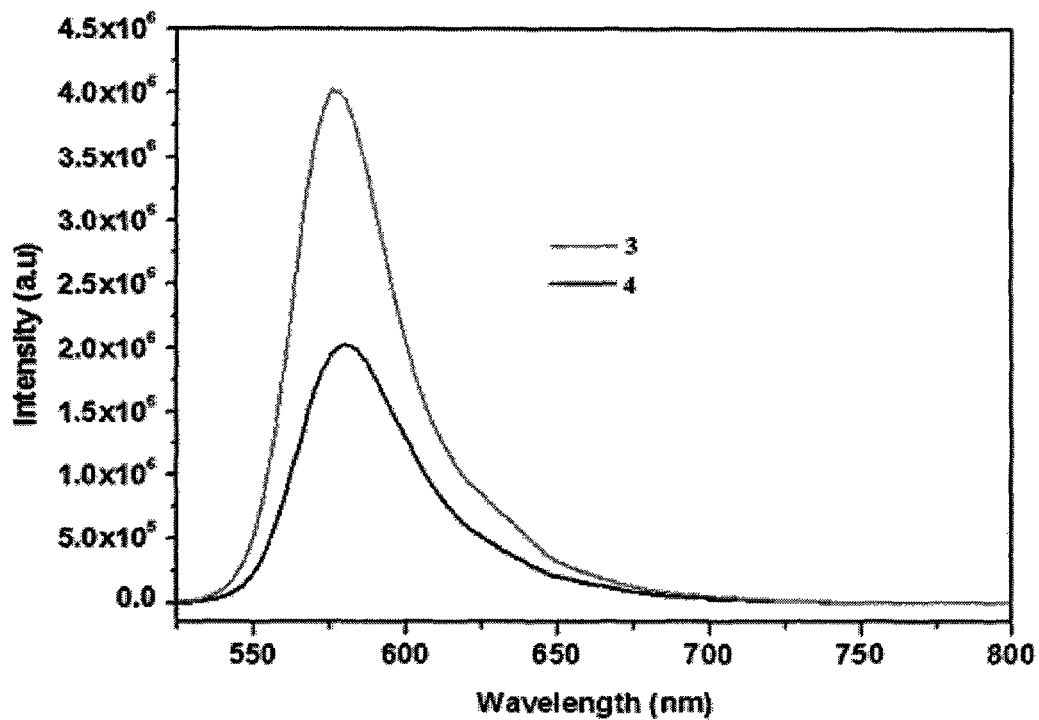

Subsequently, oxime reaction between alginate and peptide 3 (1:2 ratio) was carried out as described in Example 7 (FIG. 9A). Consistent with the previous results obtained with peptide 1, the HPLC analysis of the reaction with peptide 3 showed significant consumption of the starting material within 2 h (FIG. 9B). The resultant fluorescently labeled conjugate, alginate-GGGK(TAMRA)GGGRGDY (conjugate 4), was dialyzed against water and lyophilized to dryness for further characterization. Initially, the absorbance spectra of peptide 3 and conjugate 4 were compared, which exhibited absorbance maxima at 559 nm (FIG. 9C), indicating that the labeled peptide is successfully conjugated to alginate. Furthermore, the fluorescence spectra of both peptide 3 and conjugate 4 showed the expected emission at ~580 nm (FIG. 9D), further confirming the attachment of the fluorophore labeled peptide to alginate. According to the fluorescence intensities of the peptide 3 and conjugate 4, after dialysis, it was calculated that ~80% of the alginate underwent oxime formation with peptide 3.

Example 9

Rheological Characterization of RGD-Immobilized Alginate

1% (w/v) solutions of the RGD-modified alginate (with peptide 1) were prepared in double-distilled water (DDW) by thoroughly mixing until clear solutions were attained. The viscoelastic behavior of the RGD-modified alginate solutions was tested on a stress-control Rheometer (TA Instruments, model AR 2000), operated in the cone-plate mode with a cone angle of 10 and a 60 mm diameter. Storage (G') and loss (G") moduli were measured in a frequency sweep range of 0.1-10 Hz. The measuring device was equipped with a temperature control unit (Peltier plate, ±0.05° C.) operated at 25° C.

Example 10

Tuning the Physical and Functional Properties of Alginate Hydrogels 10.1 Selective Modification of Alginate Having optimized conditions for the selective oxime conjugation of various polysaccharides and aminoxy peptides, the strategy of linking RGD to the reducing end of alginate (Alg-RGD-E), while maintaining the carboxylic acid groups on the uronic acid monomers free for calcium cross linking to form a hydrogel, was applied. Attachment of RGD peptide, known as a potent and selective ligand of the $\alpha_v\beta_3$ integrin receptor (Ruoslahti, 1996; Sapir, 2011), has been shown to improve the alginate hydrogel as a cell matrix in tissue engineering (Re'em, 2010; Shachar, 2011; Sapir, 2011).

With this, site-selectively modified alginate-RGD conjugate was synthesize and its rheological and biofunctional properties were examined in comparison to RGD linked randomly to the alginate chains via carbodiimide chemistry (Alg-RGD-R). To achieve this, the developed oxime conjugation conditions between negatively charged alginate (Mn ~32 kD) and peptide 1 were employed to successfully obtain alginate-RGD conjugate. Notably, the chemistry was performed on gram quantities, which enabled to study the viscoelastic and cell adhesion properties of the resultant conjugates.

10.2 Characterization of Functional Properties of Alginate Hydrogels

Figure 10A:
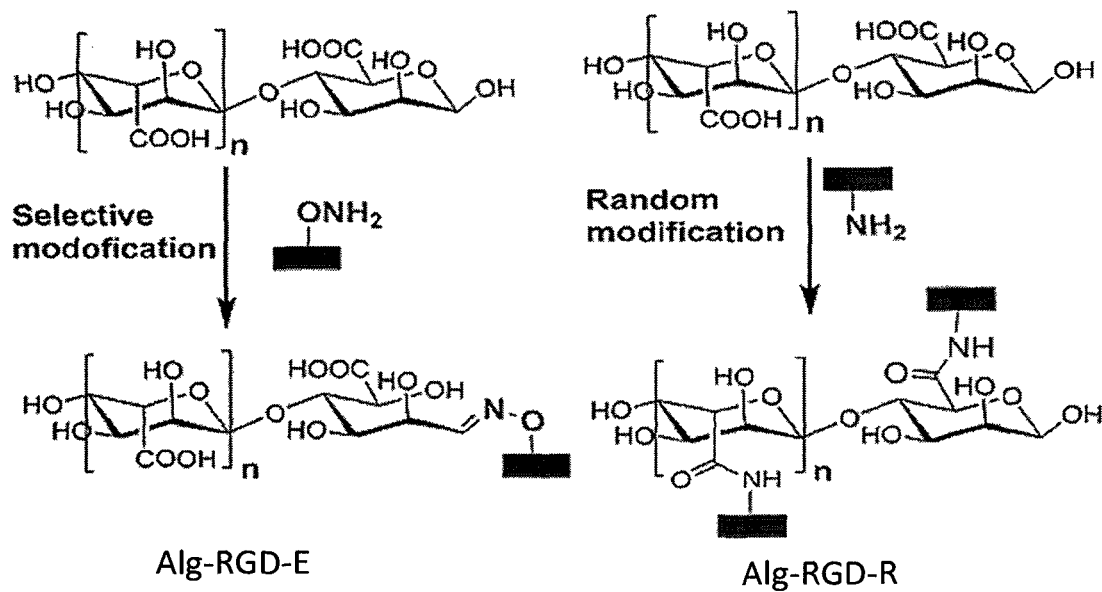
FIGS. 10A-C illustrate characterization of two modified RGD-alginate materials: (A) alginate selectively modified by the oxime chemistry at the reducing end (Alg-RGD-E) and alginate randomly modified by the carbodiimide chemistry (Alg-RGD-R); (B) and (C) show representative mechanical spectra of RGD-modified alginate solutions and of calcium crosslinked RGD-modified alginate, respectively. The small-deformation oscillatory measurements are presented in terms of the storage modulus G' and the loss modulus G", as a function of angular frequency.
Figure 10B:
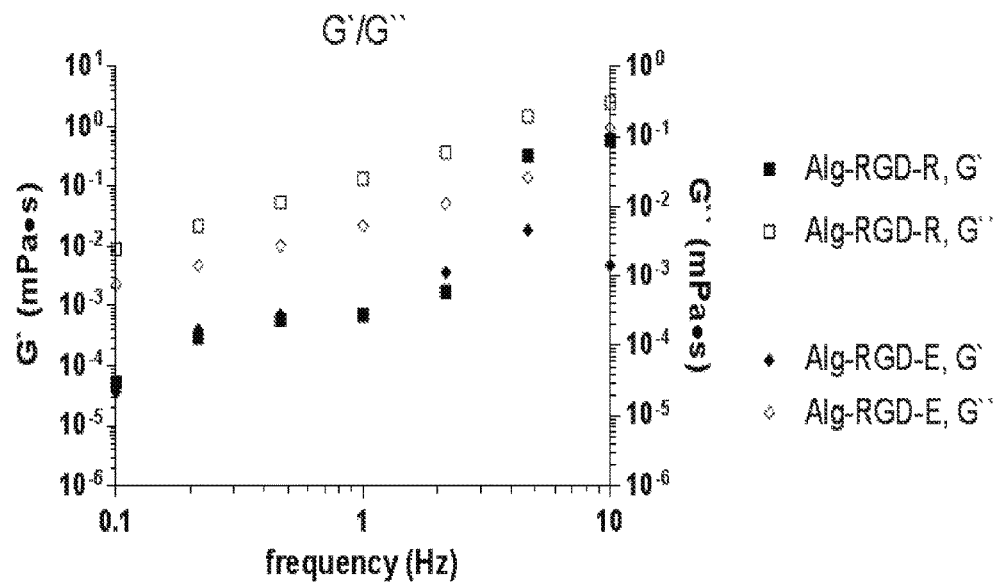
Figure 10C:
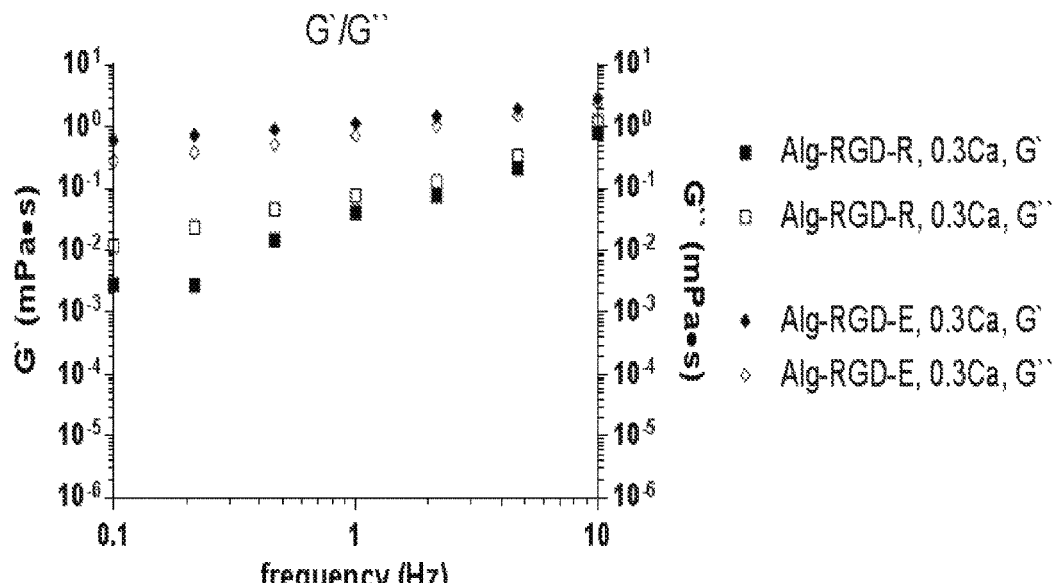

Having both Alg-RGD-E and Alg-RGD-R (FIG. 10A) materials in hand, the viscoelastic properties of 1% (w/v) solutions of RGD-modified alginates before and after cross-linking with 0.3% (w/v) hemi-calcium gluconate were compared (FIGS. 10B and 10C, respectively). For the non-cross-linked solutions (FIG. 10B), the mechanical spectra revealed loss modulus G" (viscous response) and storage modulus G' (elastic response) values that were closely related for the two RGD-modified polymers. However, after crosslinking with calcium ions, the materials displayed different mechanical spectra depending on the type of chemistry used to conjugate the RGD peptide to alginate (FIG. 10C). The mechanical spectra of Alg-RGD-E revealed a typical behavior of hydrogel, where G' is greater than G", while under the same conditions (calcium ion concentration, temperature), the Alg-RGD-R demonstrated a mechanical spectrum typical for a macromere suspension, however without reaching the gel critical point (G" is greater than G' in all frequencies). These results could be due to the unavailability of the carboxylic acid moieties on the randomly modified Alg-RGD-R for calcium crosslinking. The remarkable one-order of magnitude greater G' values for the Alg-RGD-E points to the formation of a stronger, more stable hydrogel, highlighting the importance of selective modification of the alginate chains on its physical properties.

10.3 Cell Seeding In Hydrogels

Human foreskin dermal fibroblasts were cultured on 75 cm$^2$ cell culture flask in 15 mL high glucose Dulbecco's Modified Eagle's Medium (DMEM), supplemented with 1% Pen-Strep, 2% L-glutamine and 10% fetal bovine serum (FBS) for 7 d, then removed from the dishes by 0.25% trypsin/EDTA and counted using the trypan blue exclusion assay. Prior to seeding in hydrogels, the cells were fluorescently labeled with PHK67 (Green Fluorescent Cell Linker Midi Kit for General Cell Membrane Labeling, #cat. MIDI67-1KT, Sigma). For seeding on hydrogel films, RGD-immobilized hydrogels (1% alginate, 0.3% D-gluconic acid, hemicalcium salt, w/v) were added to a 48-well plate, sterilized by UV light for 30 min, and dried at RT for 2 h. Then, 25,000 cells were added to the wells, and incubated for 24 h. For cell encapsulation, the hydrogel was prepared as follows: RGD-immobilized alginates were dissolved in double distilled water (DDW) to obtain a 2.5% (w/v) solution, and then the alginate was cross-linked by adding D-gluconic acid, hemicalcium salt, while homogenizing the mixture to achieve a uniform cross-linking of the alginate. The final concentration of alginate and calcium ions in resultant hydrogel was 2.0 and 0.6% (w/v), respectively. 100 μL of cell suspension in a medium containing 4×105 cells were mixed with 100 μL of the hydrogel prepared above, then placed in the well of a 48-well plate and incubated for 2 h, in a humidified atmosphere of 5% $CO_2$ and 95% air, at 37° C. Then, additional 0.5 mL of culture medium was added per each well. The medium was replaced every 2 days.

10.4 Fibroblast Adhesion to the RGD-Immobilized Alginate Hydrogels

Figure 11A:
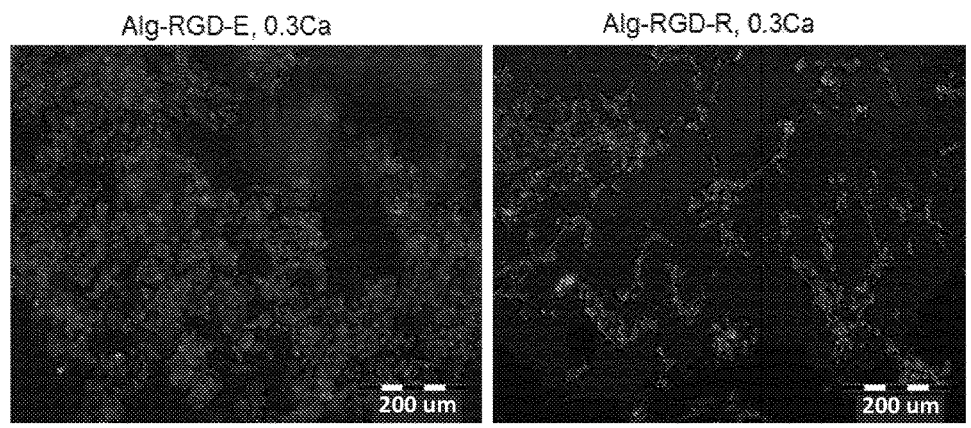
FIGS. 11A-C illustrate cell behavior in RGD-modified Alg-RGD-E and Alg-RGD-R hydrogels: (A) Cell adhesion visualized by confocal microscopy: left panel-Alg-RGD-E and right panel-Alg-RGD-R. PHK67 (green)-prestained cells were seeded on hydrogel films, and 24 h after visualized by fluorescent microscopy; (B) DNA content (left panel) and metabolic activity (right panel) of the cell-seeded hydrogels. P (interaction, two-way ANOVA, DNA content)=0.0078; P (interaction, two-way ANOVA, metabolic activity)=0.0024; *-p<0.05; and (C) Cyclin D1 (upper panel) and p21$^{cip1}$ expression (lower panel) levels in cell-seeded hydrogels, analyzed by qPCR. *-p<0.05.
Figure 11B:
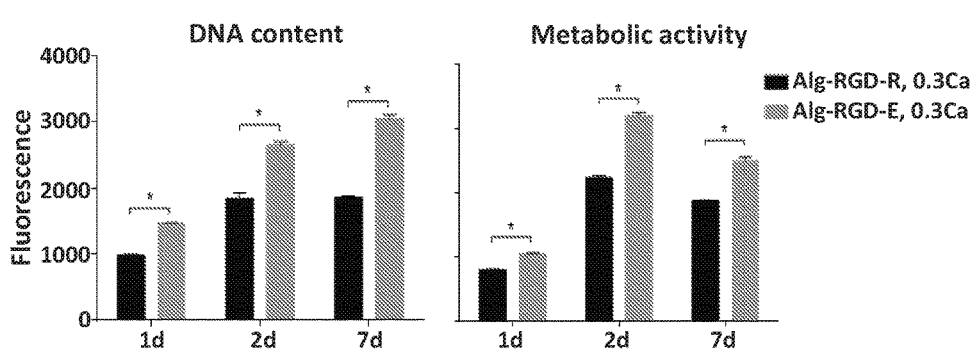

Next, cell behavior was examined (adhesion, spreading, proliferation) within the two types of RGD-modified alginate hydrogels. Fibroblast adhesion to the RGD-immobilized alginate hydrogels was characterized by strong interactions with the matrix and resistance to washing by the medium. Following cell adhesion, the fibroblasts displayed a spread-out, flat morphology in both of the RGD-modified hydrogels within 24 hours (FIG. 11A). However, in the hydrogels prepared from the Alg-RGD-E the presence of a greater cell number was observed. This has been further substantiated by the quantitative assays for DNA content and metabolic activity, where significantly higher values in both assays were observed in cells grown in Alg-RGD-E compared to Alg-RGD-R hydrogels (i.e., for DNA content: ~3000 FU (fluorescence units) vs. ~2000 FU, and for metabolic activity: ~2500 FU vs. ~2000 FU, for Alg-RGD-E and Alg-RGD-R, respectively, at 7 days) (FIG. 11B).

Figure 11C:
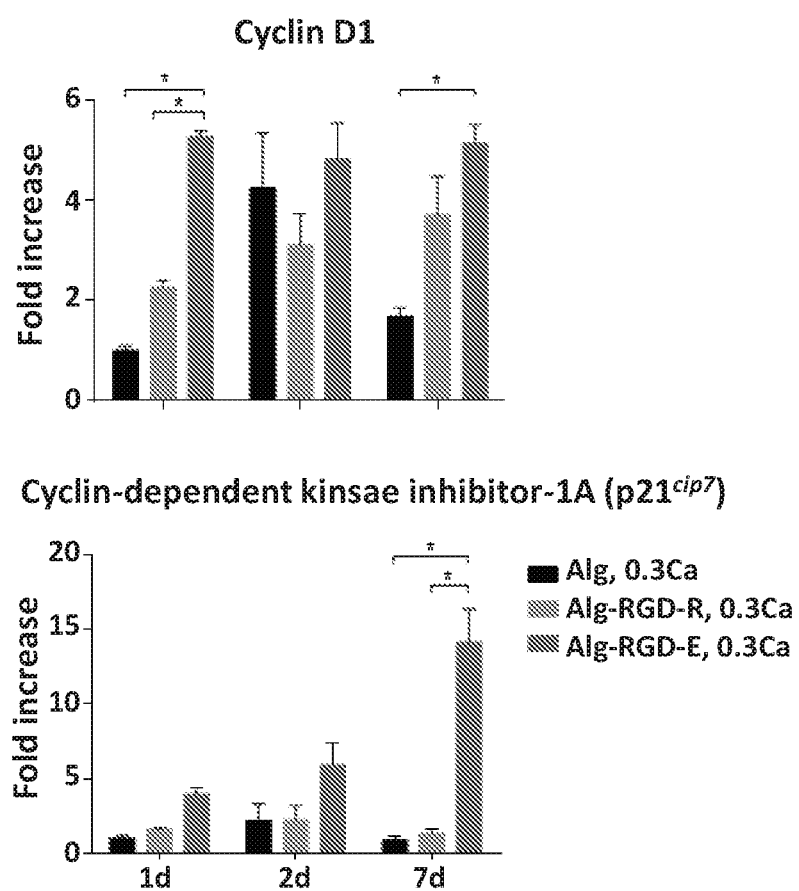

Cell adhesion and integrin binding are known to induce several intracellular signaling pathways, leading to induction of genes associated with entrance to and progression through G1 phase of cell cycle, towards DNA replication and mitosis (Assoian, 2008; Roovers, 2000). Thus, expression of key genes critical to G1 progression was examined: Cyclin D1 and cyclin-dependent kinase inhibitor-1A ($p21^{cip1}$) following the cell growth within Alg-RGD-E or Alg-RGD-R hydrogels. At day 1 and 7 of cultivation, cells grown in Alg-RGD-E hydrogels showed significantly higher levels of Cyclin D1 (FIG. 11C). Moreover, cells grown in Alg-RGD-E hydrogels exhibited significant upregulation of $p21^{cip1}$ at day 7 compared to Alg-RGD-R hydrogels. The observed upregulation of Cyclin D1 and $p21^{cip1}$ strongly suggests that significantly higher proportion of cells are in the G1 phase of cell cycle and coursed towards proliferation, further confirming the DNA content and metabolic activity results (Roovers, 2000; Bottazzi, 1999). Taken together, these results point to the superiority of the Alg-RGD-E hydrogels to maintain/encapsulate the seeded cells and provide a more favorable microenvironment for cell growth, most likely due to the more efficient crosslinking process to form a hydrogel.

10.5 Cellular DNA Content and Metabolic Activity

The DNA content of cell constructs at various time-points was determined by the Hoechst 33258 assay. Each cell construct was transferred to an eppendorf tube and 300 μL, of 4% (w/v) sodium citrate in PBS was added for dissolving the alginate hydrogel and releasing cells. Following 10 min incubation at RT with shaking, the tubes were centrifuged at 2400×g for 10 min, 4° C. The cell pellet was resuspended in 0.02% (w/v) sodium dodecyl sulfate in saline-sodium citrate, pH 7.0 (150 mM NaCl, 15 mM sodium-citrate) and incubated for 1 h at 37° C. for cell lysis. Then, Hoechst 33258 solution (2 μg/mL) was added and the mixture was incubated for 10 min at 37° C. Fluorescence was read using a microplate reader (Synergy™ Mx, BIO TEK Instruments, Winooski, Vt.) at 352/461 nm (excitation/emission). Cell viability was evaluated by PrestoBlue™ assay (Life Technologies). The constructs were incubated with 1 mL of 10% PrestoBlue™ working solution in DMEM medium with no additives for 2 h. Aliquots of PrestoBlue containing medium (300 mL) were placed in a 96-well plate and the fluorescence was measured (excitation 540 nm, emission 590 nm) using a plate reader Synergy™ Mx (BIO TEK Instruments, Winooski, Vt.). Cell-free hydrogels were used as blanks.

10.6 RNA Extraction and qPCR

The mRNA levels of CyclinD1 and $p21^{cip1}$ were quantified by real-time quantitative PCR. At indicated time-points, total RNA was isolated using the EZ-RNA purification kit (Biological Industries, Beit Haemek, Israel), and 500 ng of RNA from each sample was reverse transcribed into cDNA using the High Capacity cDNA Reverse Transcription Kit (Applied Biosystems, Foster City, Calif.). For gene expression analysis, mRNA levels were determined by real-time PCR using StepOnePlus™ Applied detection system (Applied Biosystems) according to the instructions of the manufacturer. Gene expression analysis was performed using TaqMan gene expression assays using GAPDH and ACTB as house-keeping genes. The primers were (abbreviation, TaqMan Gene Expression Assay ID): glyceraldehyde-3-phosphate dehydrogenase (GAPDH, Hs99999905-m1), Cyclin D1 (CCND1, Hs00765553-m1), $p21^{cip1}$ (CDKN1A, Hs00355782-m1), Actin Beta (ACTB, Hs99999903-m1). Results were normalized to cell constructs grown in unmodified alginate hydrogel for 24 h.

Example 11

Oxime Reaction Between Peptide 1 and Hyaluronan Sulfate

Figure 12:
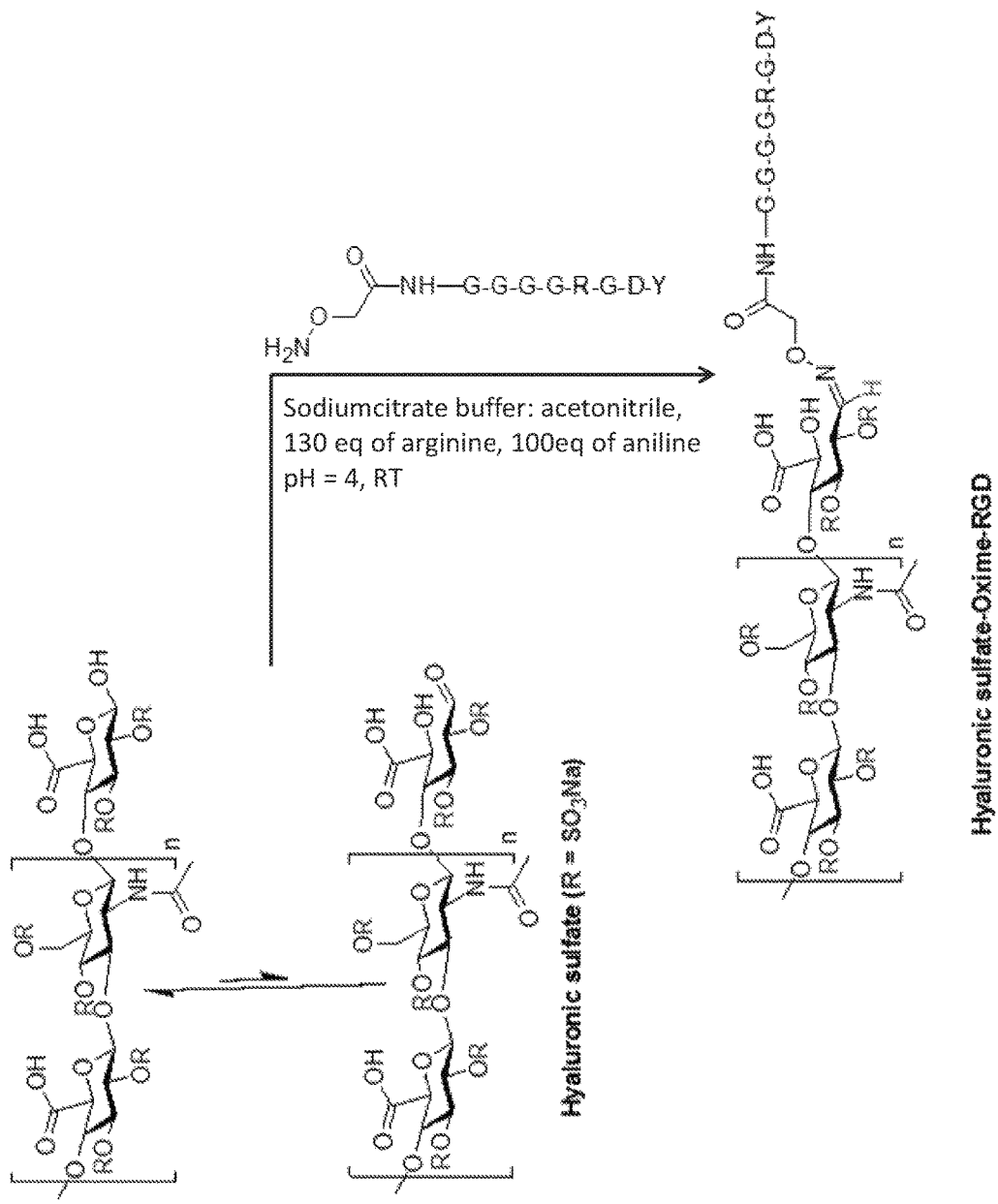
FIG. 12 is a schematic representation of oxime conjugation reaction of RGD-ONH$_2$ with hyaluronan sulfate.
Figure 13:
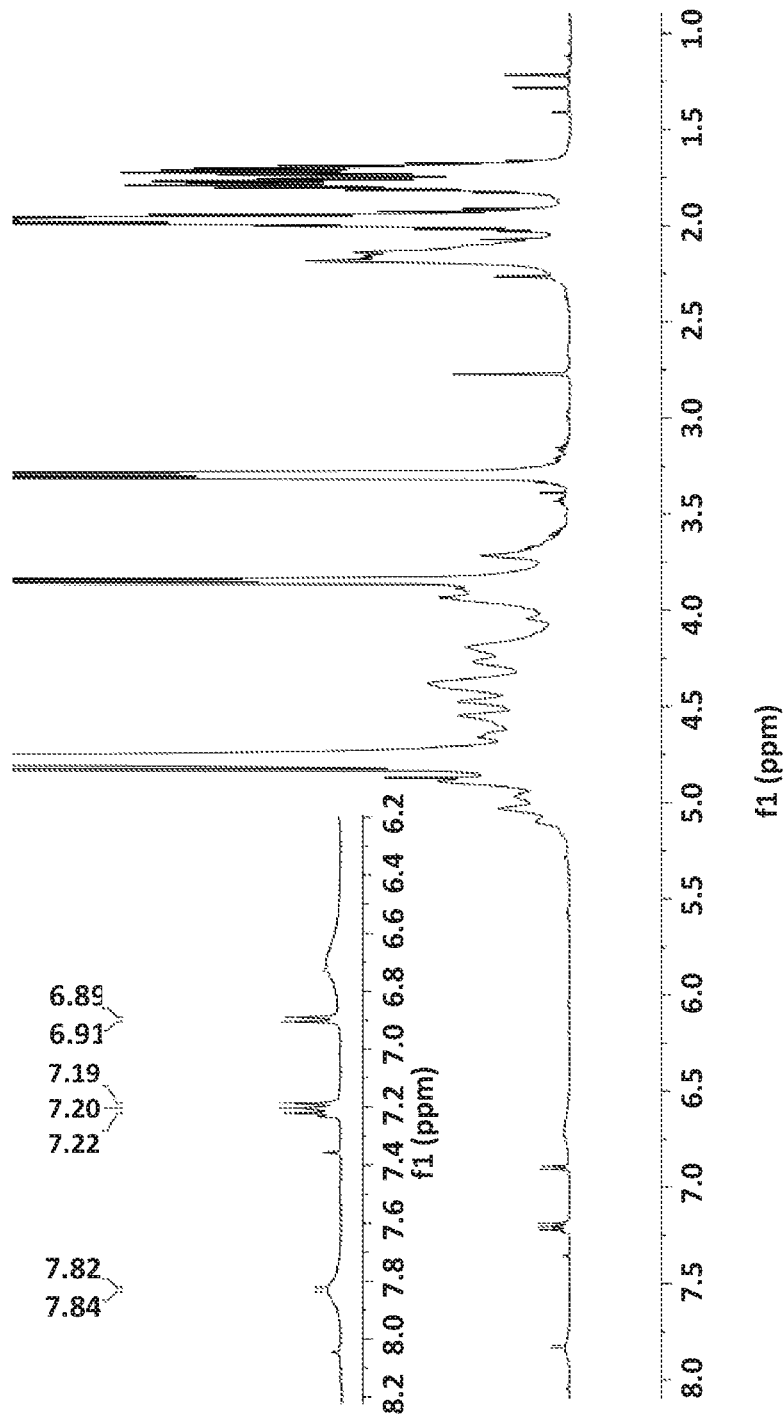
FIG. 13 is a graph showing the $^1$H NMR analysis of the RGD-oxime-hyaluronan sulfate conjugate.

Oxime conjugation reaction on hyaluronan sulfate with RGD-ONH$_2$ model peptide 1 was examined under the conditions established for hyaluronic acid (hyaluronan) in Example 4 (FIG. 12). $^1$H NMR analysis (FIG. 13) of the reaction mixture after dialysis showed the conjugate formation via anticipated oxime bond, as can be seen in the oxime characteristic peaks at 7.2 ppm and 7.8 ppm in the $^1$H NMR spectrum.

Figure 14:
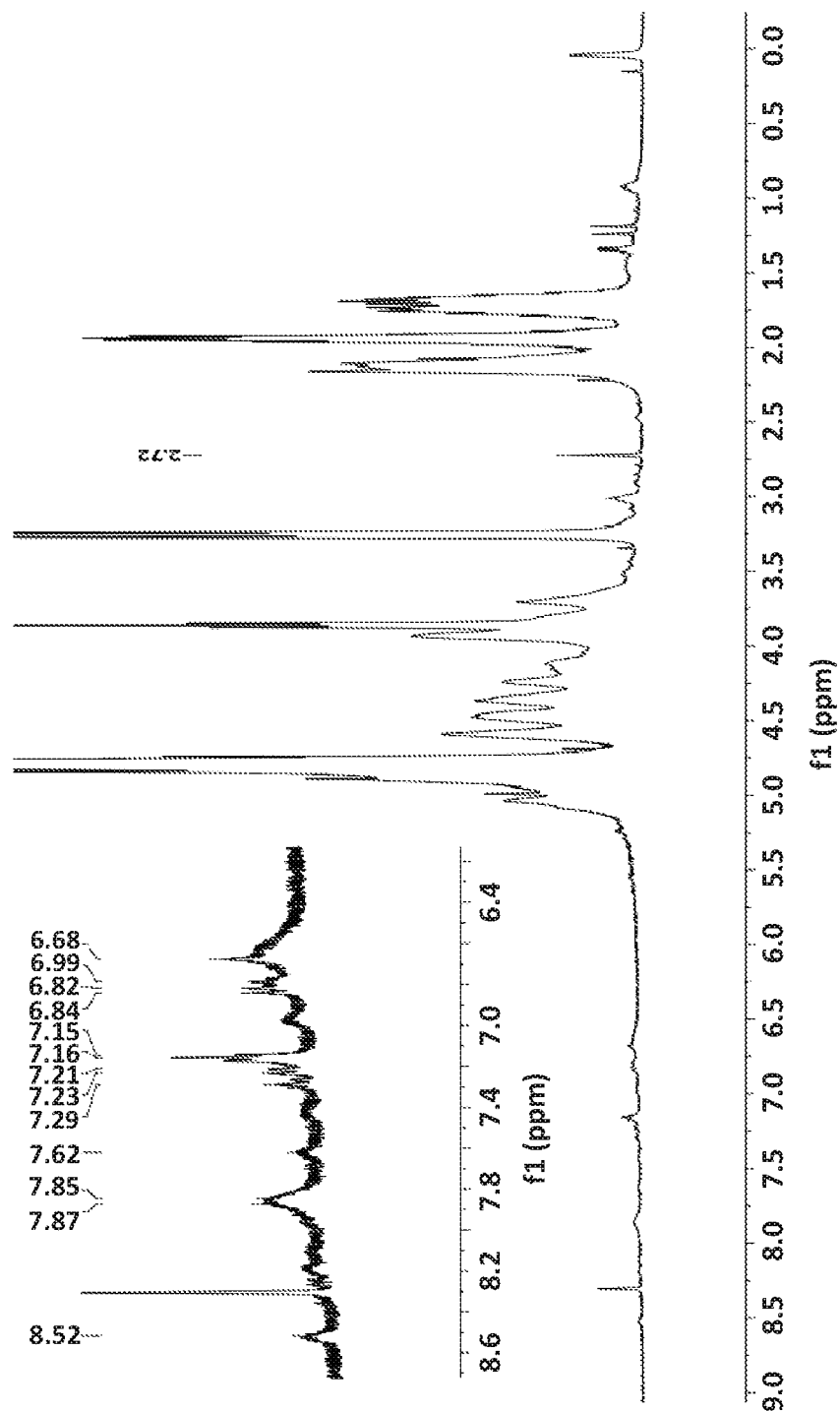
FIG. 14 is a graph showing the $^1$H NMR analysis of the NLS-TAMRA-oxime-hyaluronan sulfate conjugate.

In order to deliver new conjugated materials, NLS modified hyaluronan sulfate conjugates were synthesized. For this, both NLS-ONH$_2$ peptide and fluorophore labelled H$_2$NO-TAMRA-NLS were prepared in order to enable following the materials in further biological studies. The success of conjugate formation was analyzed with the $^i$H NMR analysis for the reaction hyaluronan sulfate with H$_2$NO-TAMRA-NLS, where the oxime characteristic peaks at 7.2 and 7.8 ppm and also peaks corresponds to aromatic protons of the fluorophore in the aromatic region i.e., from 6.8-8.0 ppm were observed (FIG. 14).

Notably, the positively charged NLS peptide attached at the end of the polysaccharide is in ionic interaction with the negatively charged sulfate groups of the hyaluronan sulfate and thus could not participate in binding with the siRNA while fabricating the nanoparticles. Accordingly, increasing the length of the linker between hyaluronan sulfate and NLS would avoid these ionic interactions and allow NLS to interact with siRNA. Therefore, a PEG linker of 75 monomer length was incorporated in between the hyaluronan sulfate and NLS.

Figure 15A:
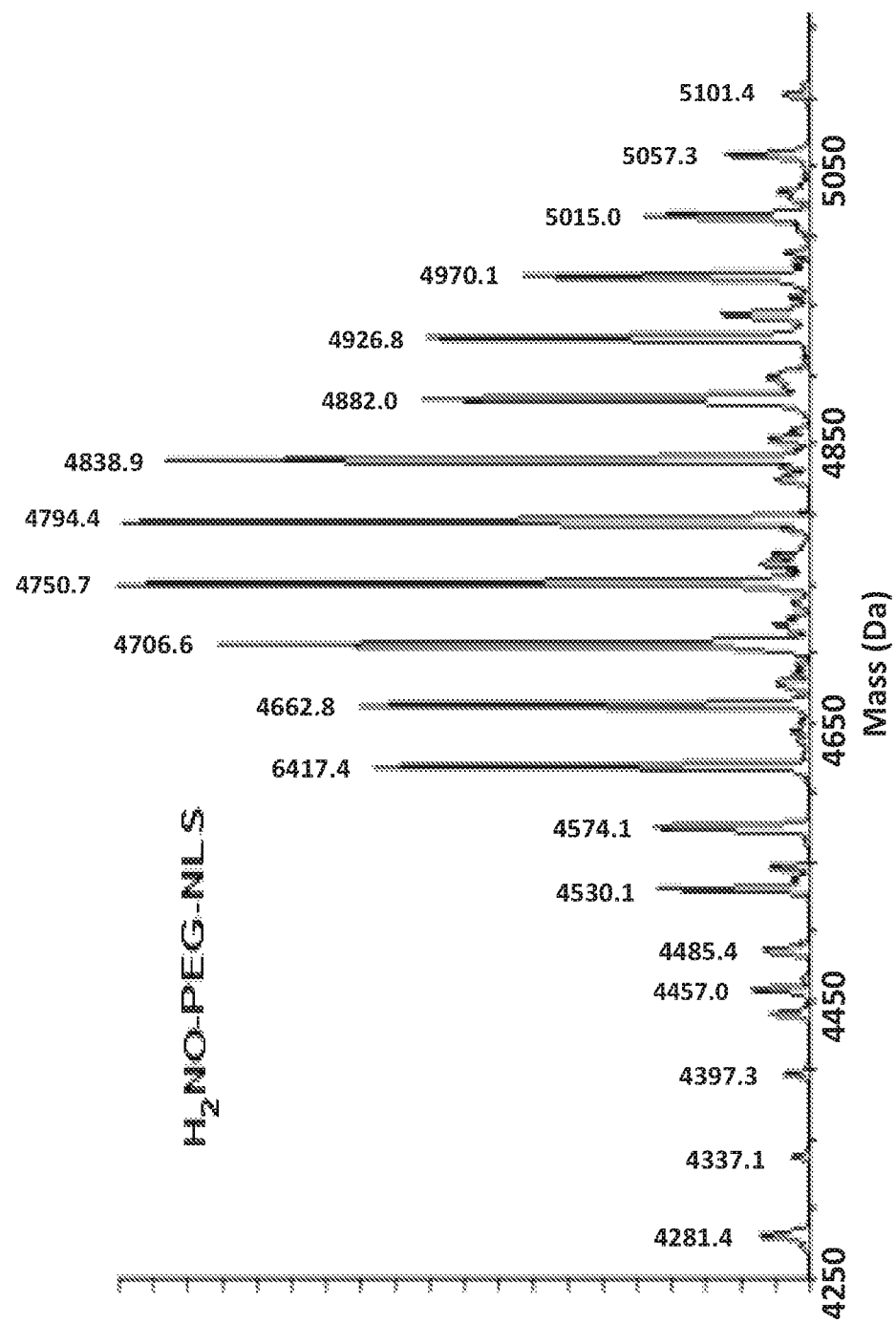
FIGS. 15A-B illustrate A) Mass analysis of H$_2$NO-PEG-NLS, and B) $^1$H NMR analysis of NLS-PEG-oxime-hyaluronan sulfate.
Figure 15B:
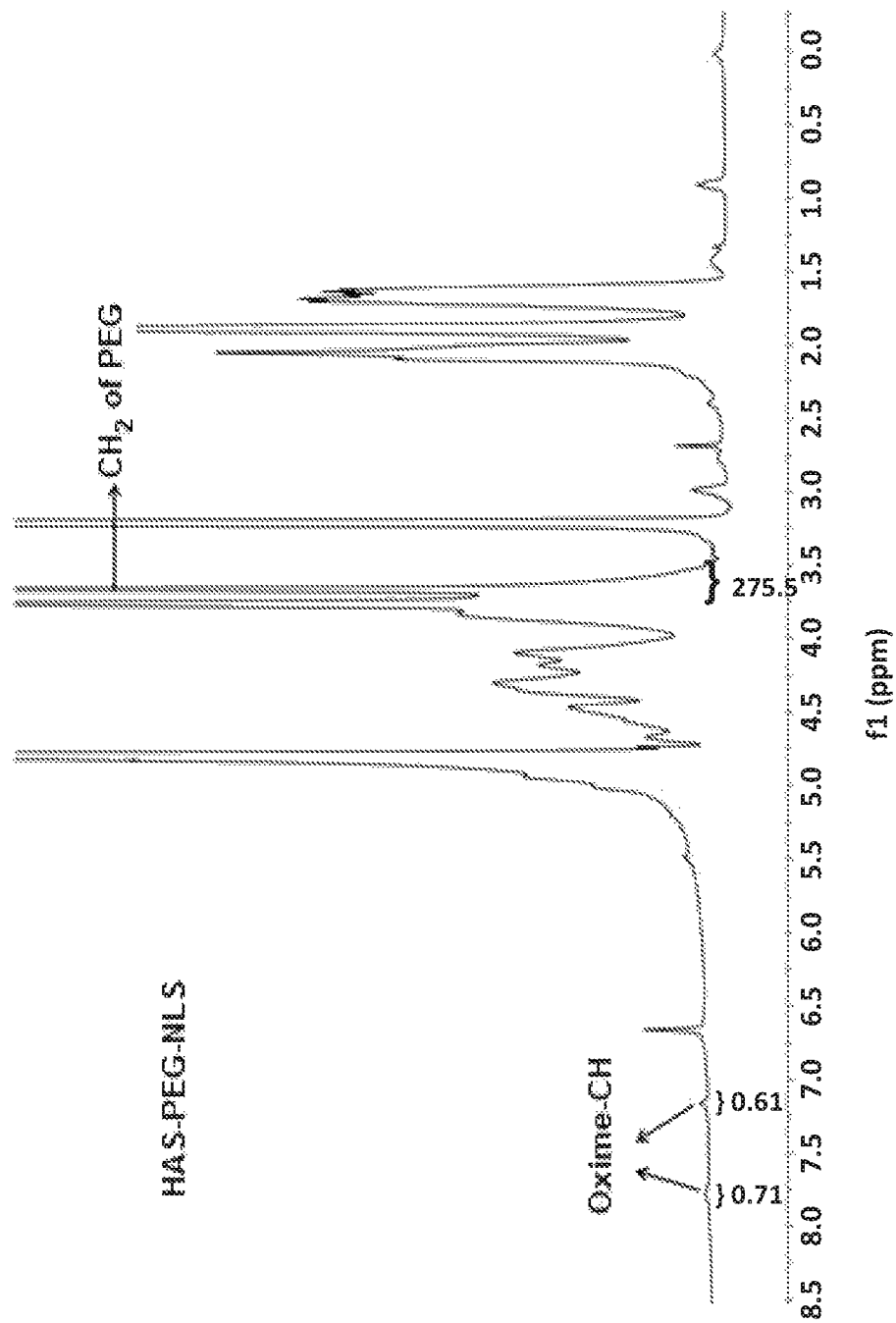

To pursue this goal, FmocNH-PEG-COOH was prepared from the commercially available NH$_2$-PEG-COOH (Mwt≈3300 Da) and coupled with resin bound NH$_2$-GGGG-PKKKRKVED by using HATU/DIEA conditions, followed by Fmoc removal and coupling with (Boc-amionoxy)acetic acid under DIC/HOBT conditions and subsequent cleavage of the peptide from the resin with the cocktail TFA:H$_2$O:TIS (95:2.5:2.5) (TIS=triisopropylsilane) to obtain H$_2$NO-PEG-NLS. The final product was purified by HPLC and analyzed by mass spectrometry (with an estimated MW of about 4800 Da: 3300 Da (PEG)+1500 Da petide) (FIG. 15A). This synthesized peptide was further subjected in an oxime conjugation reaction with hyaluronan sulfate and the product formation was analyzed by ¹H NMR spectroscopy (FIG. 15B).

Example 12

Oxime Reaction Between RGD+HBP-ONH₂ Peptide and Alginate

Figure 16:
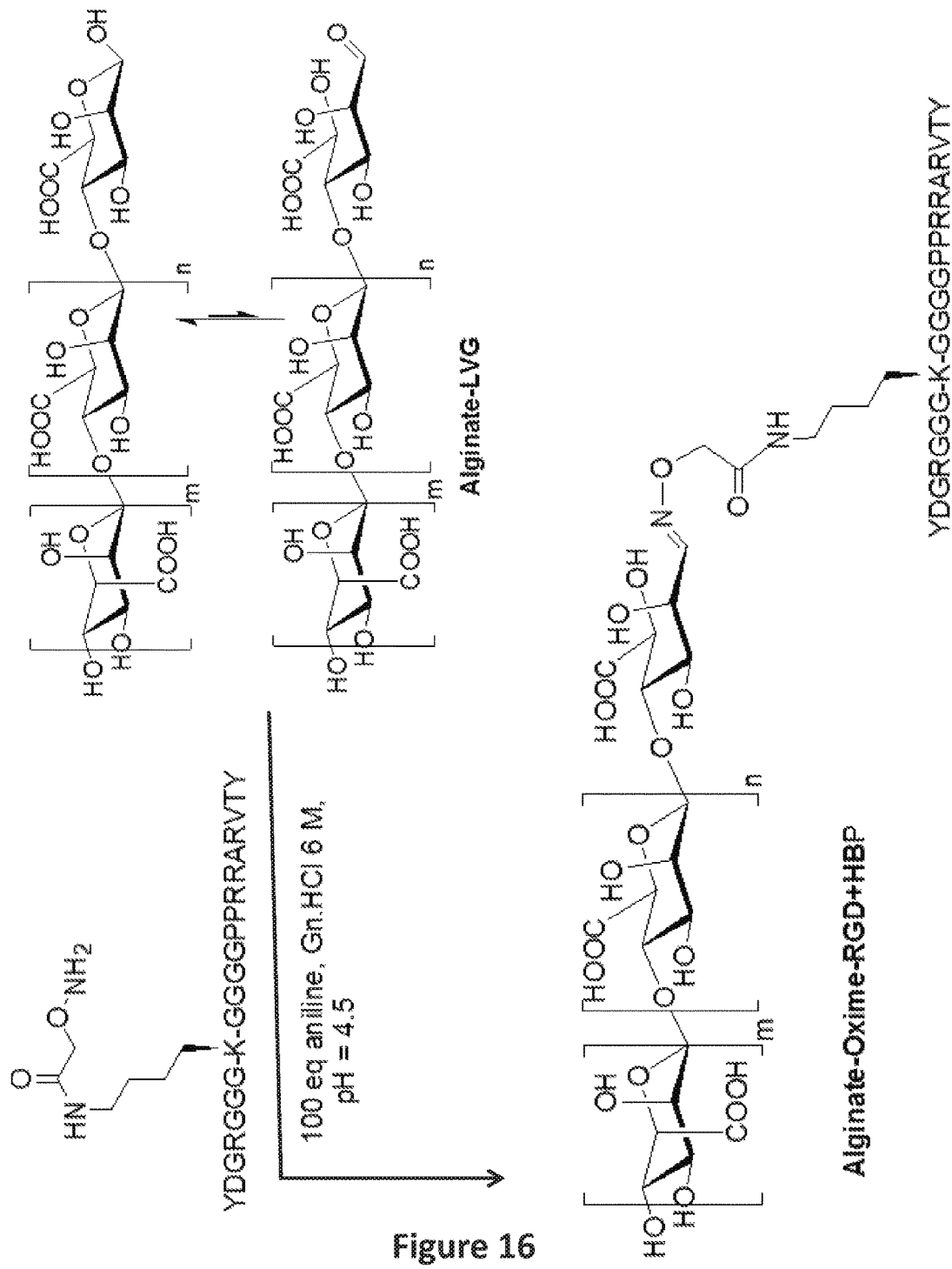
FIG. 16 is a schematic representation of oxime conjugation reaction between alginate and RGD+HBP-ONH$_2$ peptide.

Next, alginate-LVG (≈100 kD), which is known to form stable hydrogels, was modified. It is known that the combination of RGD and HBP significantly enhances the cell proliferative properties of the resultant bioconjugate material. Therefore, a petide in which both RGD and HBP are assembled as one peptide having an aminoxy functionality YDGRGGGG-(K-ONH₂)-GGGGSPPRRARVTY(RGD+HBP)-ONH₂), was synthesized. Subsequently, this peptide (1.5 eq.) was employed in the oxime conjugation reaction with alginate (1 eq.) as illustrated in FIG. 16.

Figure 17A:
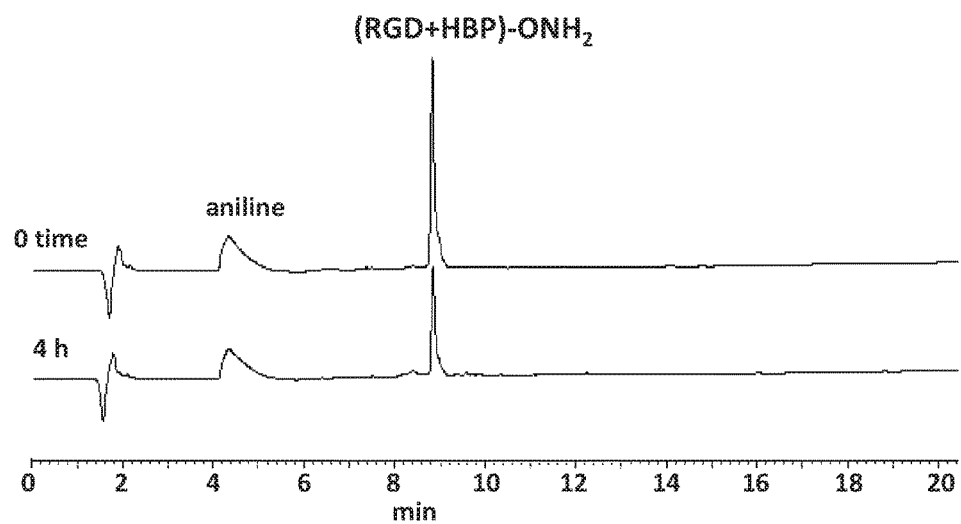
FIGS. 17A-B represent oxime conjugation reaction for alginate and RGD+HBP peptide: (A) shows an HPLC analysis of oxime conjugate reaction between Alginate and RGD+HBP peptide; and (B) shows an $^1$H NMR spectrum of Alginate-oxime-RGD+HBP conjugate.
Figure 17B:
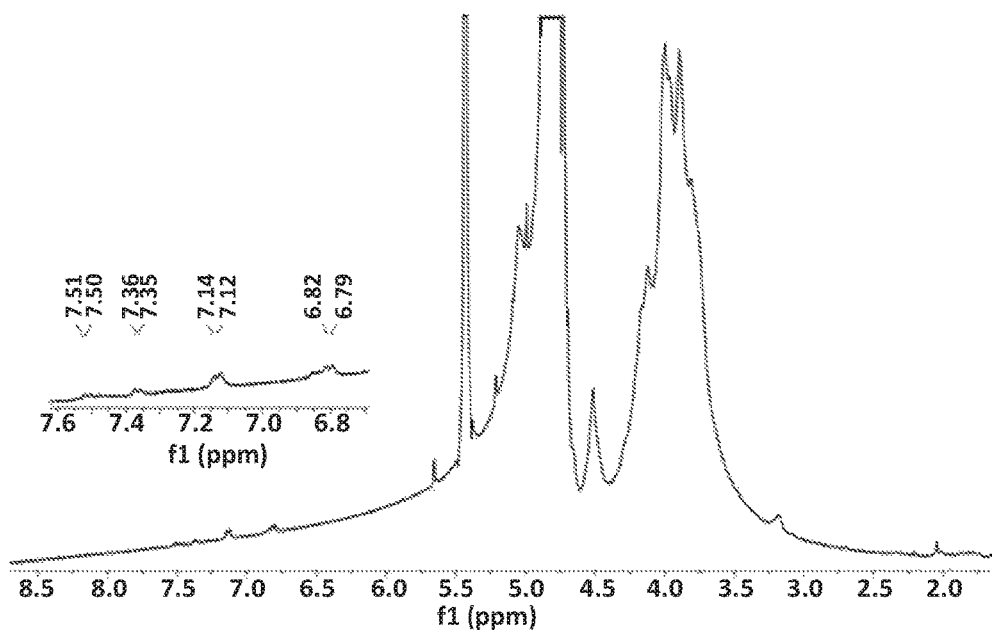

The progress of the reaction was monitored by HPLC based on the decreasing intensity of RGD+HBP-ONH₂ peak, wherein the peak corresponding to RGD+HBP-ONH₂ has attained saturation within 4 h, suggesting the completion of the reaction in 4 h (FIG. 17A). Then, the reaction mixture was dialyzed against water for two days and freeze-dried. Further, the ¹H NMR analysis confirmed the conjugate formation with the characteristic peaks of oxime at 7.3 and 7.5 ppm (FIG. 17B).

REFERENCES

Alsberg et al., *J. Dent. Res.* 2001, 80, 2025-2029;
Assoian et al., *Trends Cell Biol.* 2008, 18, 347-352;
Benediktsdottir et al., *Carbohydr. Polym.* 2012, 90, 1273-1280;
Bosker et al., *Macromolecules* 2003, 36, 1982-1987;
Bottazzi et al., *J. Cell Biol.* 1999, 146, 1255-1264;
Dirksen et al., *Angew. Chem. Int. Ed.* 2006, 45, 7581-7584;
Dirksen et al., *Bioconjugate Chem.* 2008, 19, 2543-2548;
Draget et al., *Carbohydr. Polym.* 1994, 25, 31-38;
Freeman et al., *Biomaterials* 2008, 29, 3260-3268;
Guerry et al., *Bioconjugate Chem.* 2013, 24, 544-549;
Mima et al., *J. Appl. Polym. Sci.* 1983, 28, 1909-1917;
Mizrahy et al., *Chem. Soc. Rev.* 2012, 41, 2623-2640;
Novoa-Carballal et al., *Chem. Commun.* 2012, 48, 3781-3783;
Raemdonck et al., *Adv. Drug Deliv. Rev.* 2013, 65, 1123-1147;
Rashidian et al., *Bioconjugate Chem.* 2013, 24, 333-342;
Re'em et al., *Biomaterials* 2010, 31, 6746-6755;
Roovers et al., *Bioessays* 2000, 22, 818-826;
Ruoslahti E., Annu. Rev. Cell Dev. Biol. 1996, 12, 697-715;
Sapir et al., *Biomaterials* 2011, 32, 1838-1847;
Schatz et al., *Macromol. Rapid Commun.* 2010, 31, 1664-1684;
Shachar et al., *Acta Biomater.* 2011, 7, 152-162;
Styslinger et al., *J. Am. Chem. Soc.* 2012, 134, 7507-7515;
Wendeler et al., *Bioconjugate Chem.* 2014, 25, 93-101;
WO 2003/024984
Zhang et al., *ACS Appl. Mater. Interfaces* 2013, 5, 10760-10766;

The invention claimed is:

1. A modified polysaccharide selectively modified at its reducing end by conjugation with a single aminoxy-Regioselective Addressable Functionalized Template (RAFT) peptide, wherein said RAFT peptide is a biologically active linear or cyclic RAFT peptide comprising the sequence GGGKGGGRGDY (SEQ ID NO: 2).

2. The modified polysaccharide of claim 1, wherein said polysaccharide is selected from chitosan, dextran, heparin, heparan sulfate, keratin sulfate, pectin, starch, hyaluronic acid, sulfated hyaluronan, alginate, alginate sulfate, and chondroitin sulfate.

3. The modified polysaccharide of claim 2, wherein said polysaccharide is alginate or alginate sulfate.

4. The modified polysaccharide of claim 2, wherein said polysaccharide is hyaluronic acid or sulfated hyaluronan.

5. The modified polysaccharide of claim 1, wherein said RAFT peptide is labeled.

6. The modified polysaccharide of claim 1, wherein said RAFT peptide comprises one or more functional units exhibiting biological activity.

7. The modified polysaccharide of claim 5, wherein said RAFT peptide is labeled with a dye or biotin.

8. The modified polysaccharide of claim 7, wherein said dye is a fluorophore label 5-carboxytetramethylrhodamine (TAMRA) linked to the lysine side chain of said RAFT peptide.

9. The modified polysaccharide of claim 2, selected from dextran GGGKGGGRGDY, and chitosan GGGK-GGGRGDY.

10. A process for the preparation of a modified polysaccharide according to claim 1, comprising conjugation of a polysaccharide with an aminoxy-functionalized peptide in the presence of aniline.

11. The modified polysaccharide of claim 6, wherein said functional units are biomolecules.

12. The modified polysaccharide of claim 11, wherein said biomolecules are peptides or oligosaccharides.

13. The modified polysaccharide of claim 3, wherein said modified polysaccharide is alginate sulfate-GGGK-GGGRGDY.

14. The modified polysaccharide of claim 4, wherein said modified polysaccharide is hyaluronic acid-GGGK-GGGRGDY.

15. The modified polysaccharide of claim 8, wherein said modified polysaccharide is alginate-GGGK(TAMRA) GGGRGDY.

* * * * *